(12) United States Patent
Hamada et al.

(10) Patent No.: US 8,741,219 B2
(45) Date of Patent: Jun. 3, 2014

(54) SAMPLE PROCESSING SYSTEM, BASE FOR SAMPLE PROCESSING SYSTEM, AND SAMPLE PROCESSING APPARATUS

(75) Inventors: Yuichi Hamada, Kobe (JP); Keisuke Kuwano, Kobe (JP)

(73) Assignee: Sysmex Corporation, Kobe (JP)

( * ) Notice: Subject to any disclaimer, the term of this patent is extended or adjusted under 35 U.S.C. 154(b) by 1175 days.

(21) Appl. No.: 12/638,695

(22) Filed: Dec. 15, 2009

(65) Prior Publication Data

US 2010/0150780 A1  Jun. 17, 2010

(30) Foreign Application Priority Data

Dec. 16, 2008 (JP) ................................. 2008-319560

(51) Int. Cl.
| | |
|---|---|
| *G01N 21/00* | (2006.01) |
| *G01N 31/00* | (2006.01) |
| *G01N 33/00* | (2006.01) |
| *G01N 35/02* | (2006.01) |
| *G01N 21/75* | (2006.01) |
| *G01N 31/22* | (2006.01) |
| *G01N 33/52* | (2006.01) |
| *G01N 35/00* | (2006.01) |

(52) U.S. Cl.
USPC ................. 422/65; 422/62; 422/63; 422/402; 422/403; 422/404; 436/47; 436/48

(58) Field of Classification Search
None
See application file for complete search history.

(56) References Cited

U.S. PATENT DOCUMENTS

| | | | |
|---|---|---|---|
| 2005/0036913 A1 | 2/2005 | Yamakawa et al. | |
| 2007/0237675 A1* | 10/2007 | Nichols et al. | 422/63 |
| 2008/0069730 A1* | 3/2008 | Itoh | 422/65 |
| 2008/0131318 A1* | 6/2008 | Nakaya | 422/63 |
| 2009/0004056 A1* | 1/2009 | Clement | 422/63 |

FOREIGN PATENT DOCUMENTS

| | | |
|---|---|---|
| JP | 2000-028620 A | 1/2000 |
| JP | 2000-118083 A | 4/2000 |
| JP | 2001-349897 A | 12/2001 |

* cited by examiner

*Primary Examiner* — Jill Warden
*Assistant Examiner* — Julie Tavares
(74) *Attorney, Agent, or Firm* — Brinks Gilson & Lione

(57) ABSTRACT

A sample processing system comprising: a transporting apparatus for transporting a sample; a plurality of sample processing apparatuses, arranged along a direction in which the sample is transported by the transporting apparatus, for processing the sample transported by the transporting apparatus; a base on which at least one of the sample processing apparatuses is placed; and a movement restricting section for restricting, on the base, a movement area within which the sample processing apparatus moves, wherein the movement restricting section allows the sample processing apparatus to move on the base so as to change orientation of the sample processing apparatus, is disclosed. A base for a sample processing system and a sample processing apparatus are also disclosed.

12 Claims, 22 Drawing Sheets

SAMPLE PROCESSING SYSTEM, BASE FOR SAMPLE PROCESSING SYSTEM, AND SAMPLE PROCESSING APPARATUS

RELATED APPLICATIONS

This application claims priority under 35 U.S.C. §119 to Japanese Patent Application No. JP2008-319560 filed on Dec. 16, 2008, the entire content of which is hereby incorporated by reference.

FIELD OF THE INVENTION

The present invention relates to a sample processing system, and particularly to a sample processing system including a plurality of sample processing apparatuses. The present invention also relates to a base used for the sample processing system including the plurality of sample processing apparatuses. Further, the present invention relates to a sample processing apparatus.

BACKGROUND OF THE INVENTION

Conventionally, there is a known sample processing system including a plurality of sample processing apparatuses. Such a sample processing system is configured to include: bases on which a sample processing apparatus is respectively placed; and a transporting apparatus for transporting samples to the sample processing apparatuses. Each sample processing apparatus can be moved on the base when a connection thereof to the transporting apparatus is released. However, when the sample processing apparatuses are moved on the base, there is a fear of the sample processing apparatuses falling off the base. Owing to this, performing maintenance work on the sample processing apparatuses is onerous.

In order to eliminate the onerosity of the maintenance work, in a sample processing system described in JP laid-open patent 2001-349897, two sample processing apparatuses are arranged to be adjacent to each other on a straight-line travel path provided on the base. The sample processing system is configured such that, when maintenance work is performed on the sample processing apparatuses, one of the two sample processing apparatuses is rectilinearly moved on the movement path in a direction along which the sample processing apparatuses are arranged. In this manner, the sample processing apparatuses can be distanced from each other, and space for the maintenance work can be obtained.

However, in the sample processing system described in JP laid-open patent 2001-349897, the movement of the sample processing apparatus is limited to rectilinear movement. For this reason, in the case where the maintenance work is to be performed on side faces, of the two sample processing apparatuses, which are opposed to each other, it is necessary to have a movement path of a substantial length in order to make a substantial distance between these two sample processing apparatuses so that sufficient space for the maintenance work can be obtained. Accordingly, there is a problem that the sample processing system is large in size.

SUMMARY OF THE INVENTION

The scope of the invention is defined solely by the appended claims, and is not affected to any degree by the statements within this summary.

A first aspect of this invention is a sample processing system comprising: a transporting apparatus for transporting a sample; a plurality of sample processing apparatuses, arranged along a direction in which the sample is transported by the transporting apparatus, for processing the sample transported by the transporting apparatus; a base on which at least one of the sample processing apparatuses is placed; and a movement restricting section for restricting, on the base, a movement area within which the sample processing apparatus moves, wherein the movement restricting section allows the sample processing apparatus to move on the base so as to change orientation of the sample processing apparatus.

A second aspect of this invention is a base on which at least one of a plurality of sample processing apparatuses for processing a sample transported by a transporting apparatus is placed, the base comprising a movement restricting section for restricting, on the base, a movement area within which the sample processing apparatus moves, wherein the movement restricting section allows the sample processing apparatus to move on the base so as to change orientation of the sample processing apparatus.

A third aspect of this invention is A sample processing apparatus, placed on a base in a movable manner, for processing a sample transported by a transporting apparatus, the sample processing apparatus comprising: a movement smoothing member for smoothing a movement of the sample processing apparatus on the base; and an inclination restricting member for restricting an inclination of the sample processing apparatus with respect to the base, wherein when the sample processing apparatus is moved to such a position that when viewed in a plan view, the sample processing apparatus partly protrudes from the base, the inclination restricting member restricts the inclination of the sample processing apparatus with respect to the base.

DETAILED DESCRIPTION OF THE PREFERRED EMBODIMENTS

Hereinafter, an embodiment of a sample processing system of the invention will be described in detail with reference to the accompanying drawings.

Figure 1:
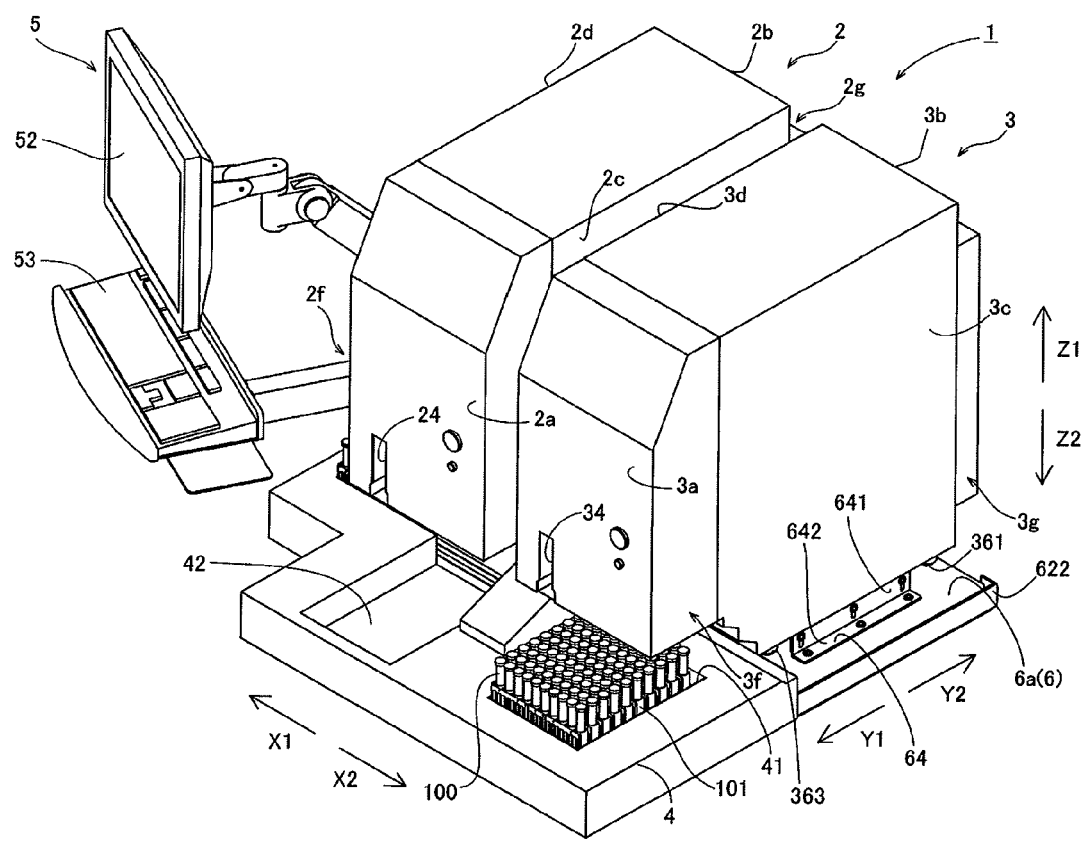
FIG. 1 is a perspective view showing an overall structure of a blood analyzer according to an embodiment of the present invention.

FIG. 1 is a perspective view showing an overall structure of a blood analyzer according to the embodiment of the present invention. FIGS. 2 to 13 illustrate in detail the respective components of the blood analyzer according to the embodiment shown in FIG. 1. First, an overall structure of a blood analyzer 1 according to the embodiment of the present invention will be described with reference to FIGS. 1 to 13. Note that the present embodiment describes a case where the present invention is applied in the blood analyzer that is an example of a sample processing system.

As shown in FIG. 1, the blood analyzer 1 according to the present embodiment includes: two measurement units that are a first measurement unit 2 and a second measurement unit 3; a sample transporting apparatus (sampler) 4 disposed in front of the first measurement unit 2 and the second measurement unit 3 (i.e., disposed on an arrow Y1 direction side); a control apparatus 5 structured as a PC (Personal Computer) that is electrically connected to the first measurement unit 2, the second measurement unit 3, and the sample transporting apparatus 4; and a base 6 for mounting thereon the first measurement unit 2 and the second measurement unit 3. Further, the blood analyzer 1 is connected to a host computer 7 (see FIG. 2) via the control apparatus 5.

Figure 2:
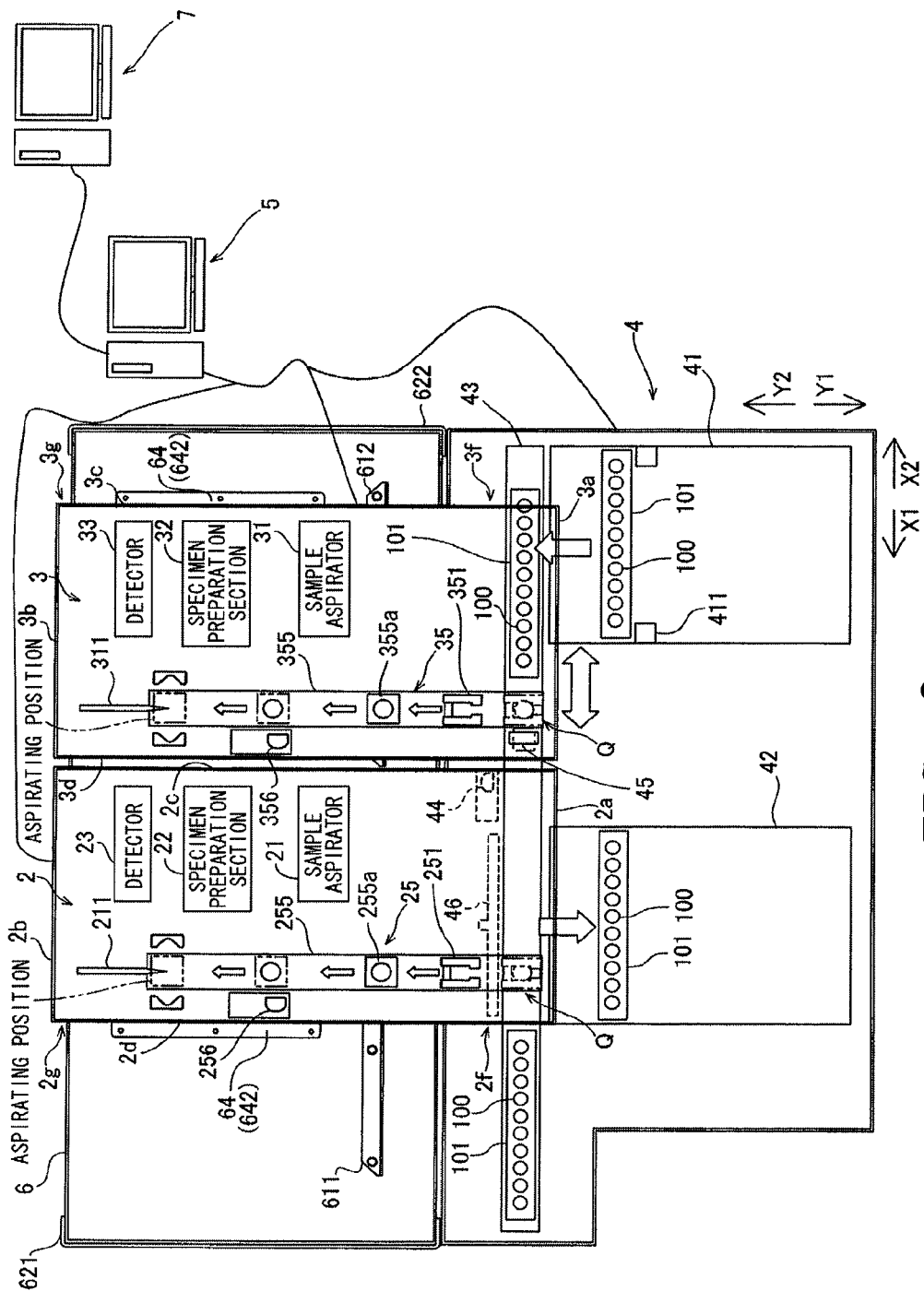
FIG. 2 schematically shows measurement units and a sample transporting apparatus of the blood analyzer according to the embodiment of the present invention.

As shown in FIGS. 1 and 2, the first measurement unit 2 and the second measurement unit 3 are arranged, along the X direction, on the base 6 so as to be adjacent to each other. The first measurement unit 2 includes: a front face 2a on a sample transporting apparatus 4 side (Y1 direction side); a back face 2b on a Y2 direction side; one side face 2c on an X2 direction side; the other side face 2d on an X1 direction side; and a bottom face 2e (see FIG. 5). The second measurement unit 3 includes: a front face 3a on the sample transporting apparatus 4 side (Y1 direction side); a back face 3b on the Y2 direction side; one side face 3c on the X2 direction side; the other side face 3d on the X1 direction side; and a bottom face 3e (see FIG. 5). The first measurement unit 2 and the second measurement unit 3 are arranged such that the one side face 2c of the first measurement unit 2 and the other side face 3d of the second measurement unit 3 are closely opposed to each other. When arranged on the base 6, the first measurement unit 2 and the second measurement unit 3 include an overhanging portion 2f and an overhanging portion 3f at the front face 2a and the front face 3a, respectively, the overhanging portions 2f and 3f protruding (on a Z1 direction side) above the sample transporting apparatus 4. The first measurement unit 2 and the second measurement unit 3 also include an overhanging portion 2g and an overhanging portion 3g at the back face 2b and the back face 3b, respectively, which protrude backward (in the Y2 direction). Accordingly, the external shape of the first and second measurement units 2 and 3 is configured so as to protrude, when viewed in a plan view, beyond the external shape of the base 6.

Figure 3:
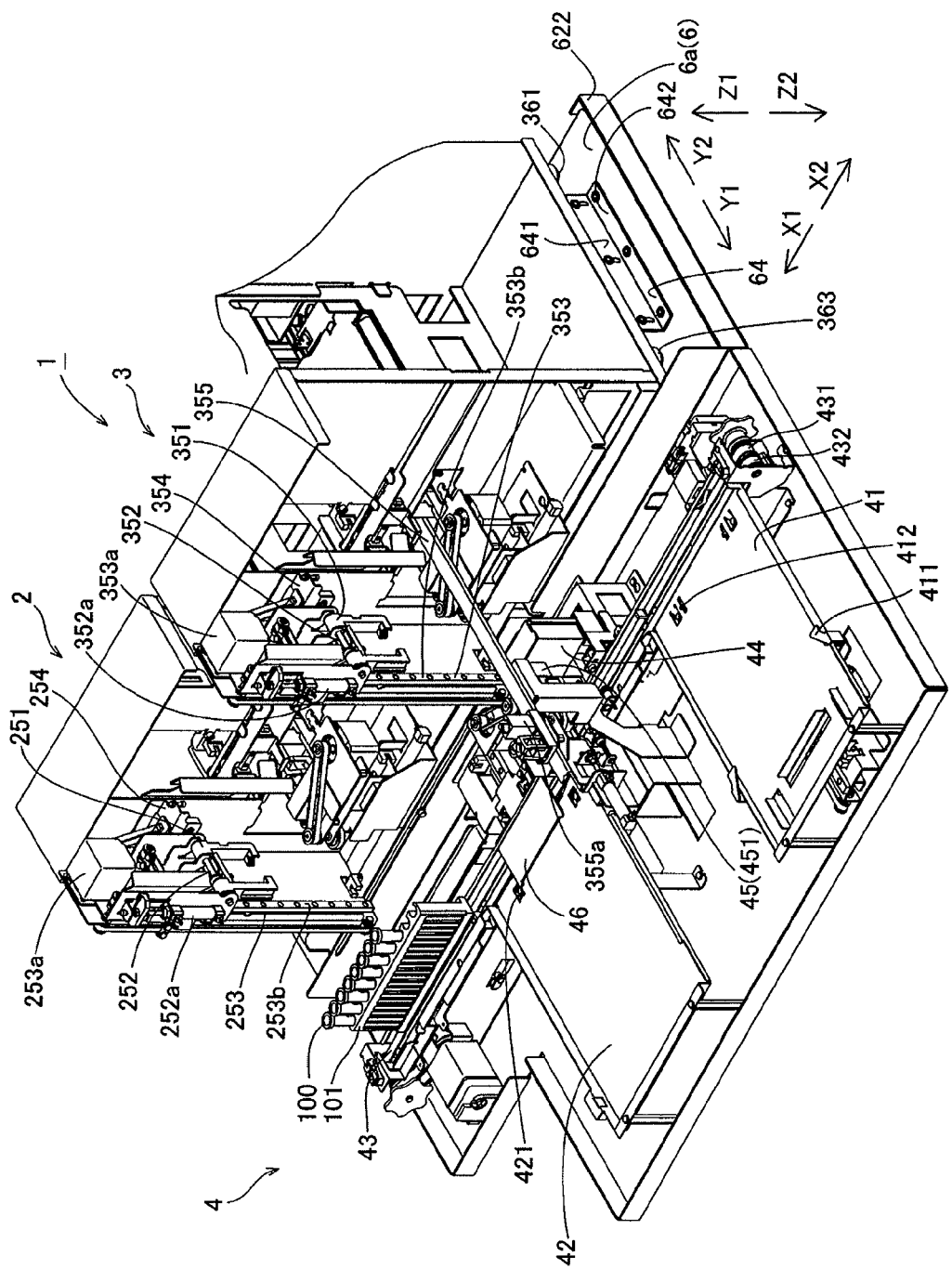
FIG. 3 is a perspective view showing internal structures of the measurement units and the sample transporting apparatus of the blood analyzer according to the embodiment of the present invention.

Further, as shown in FIGS. 1 to 3, the first measurement unit 2 and the second measurement unit 3 are measurement units of practically the same type, which are arranged so as to be adjacent to each other. To be specific, in the present embodiment, the second measurement unit 3 uses the same measurement principle as that of the first measurement unit 2 to measure a sample for the same measurement item as that of the first measurement unit 2. The second measurement unit 3 further performs measurement for measurement items for which the first measurement unit 2 does not perform measurement. As shown in FIG. 2, the first measurement unit 2 includes: a sample aspirator 21 for aspirating a blood sample from a sample container (test tube) 100; a specimen preparation section 22 for preparing a detection specimen from the blood aspirated by the sample aspirator 21; and a detector 23 for detecting blood cells from the detection specimen prepared by the specimen preparation section 22. Also, the second measurement unit 3 includes: a sample aspirator 31 for aspirating a blood sample from a sample container (test tube) 100; a specimen preparation section 32 for preparing a detection specimen from the blood aspirated by the sample aspirator 31; and a detector 33 for detecting blood cells from the detection specimen prepared by the specimen preparation section 32.

Further, the first measurement unit 2 includes: a loading opening 24 (see FIG. 1) through which a sample container 100 accommodated in a rack 101 (see FIG. 4) transported by the sample transporting apparatus 4 is loaded into the first measurement unit 2; and a sample container transporter 25 for loading the sample container 100 from the rack 101 into the first measurement unit 2, and for transporting the sample container 100 to an aspirating position (see FIG. 2) of the sample aspirator 21. Also, the second measurement unit 3 includes: a loading opening 34 (see FIG. 1) through which a sample container 100 accommodated in the rack 101 (see FIG. 4) transported by the sample transporting apparatus 4 is loaded into the second measurement unit 3; and a sample container transporter 35 for loading the sample container 100 from the rack 101 into the second measurement unit 3, and for transporting the sample container 100 to an aspirating position (see FIG. 2) of the sample aspirator 31.

As shown in FIG. 2, the sample aspirator 21 (31) includes a piercer 211 (311). The tip of the piercer 211 (311) is formed so as to be able to penetrate (pierce) through a sealing cap of the sample container 100. Further, the piercer 211 (311) is configured to move in vertical directions (an arrow Z1 direction and an arrow Z2 direction) through an operation of a piercer drive section that is not shown.

The detector 23 (33) is configured to perform RBC detection (detection of red blood cells) and PLT detection (detection of platelets) by the sheath flow DC detection method, and to perform HGB detection (detection of hemoglobin in blood) by the SLS-hemoglobin method. The detector 23 (33) is also configured to perform WBC detection (detection of while blood cells) by flow cytometry using semiconductor laser. Detection results obtained by the detector 23 (33) are transmitted to the control apparatus 5 as measurement data (measurement results) of the sample. Note that the measurement data is used as a basis for final analysis results provided to a user (such as a red blood count, platelet count, amount of hemoglobin, white blood count, and the like).

As shown in FIG. 3, the sample container transporter 25 (35) includes: a hand part 251 (351) capable of holding a sample container 100; an opening/closing part 252 (352) capable of opening/closing the hand part 251 (351); a vertically moving part 253 (353) for rectilinearly moving the hand part 251 (351) in vertical directions (i.e., arrow Z directions); and an agitator 254 (354) for moving the hand part 251 (351) in the vertical directions (arrow Z directions) in a swinging manner. Further, as shown in FIG. 2, the sample container transporter 25 (35) has: a sample container moving part 255 (355) for holding, at a sample setting part 255a (355a), a sample container 100 that is obtained from the rack 101 by the hand part 251 (351), and horizontally and rectilinearly moving the sample container 100 in the arrow Y2 direction to the aspirating position of the sample aspirator 21 (31); and a bar code reader 256 (356).

The hand part 251 and the hand part 351 are provided in the overhanging portion 2f of the first measurement unit 2 and the overhanging portion 3f of the second measurement unit 3, respectively, and are arranged above a transporting path (i.e., on the arrow Z1 direction side) on which the rack 101 is transported by the sample transporting apparatus 4. The hand part 251 (351) is configured to, when a sample container 100 has been transported by the sample transporting apparatus 4 to a below-described removal position Q (see FIG. 2), move downward (in the arrow Z2 direction) and then be caused by the opening/closing part 252 (352) to open and close to hold the sample container 100 accommodated in the rack 101.

Further, the hand part 251 (351) is capable of moving the held sample container 100 upward (in the Z1 direction) to remove the sample container 100 from the rack 101, and agitating the blood contained in the held sample container 100 by being moved in a swinging manner by the agitator 254 (354) (e.g., 10 reciprocatory swinging movements). The hand part 251 (351) is configured to move, after the agitation has ended, downward (in the Z2 direction) and then be caused by the opening/closing part 252 (352) to release the holding of the sample container 100. To be specific, the hand part 251 (351) is configured to set the held sample container 100 into the sample setting part 255a (355a) that has been moved from the back side (Y2 direction side) by the sample container moving part 255 (355) so as to be disposed in a vertically downward position (on the Z2 direction side) with respect to the hand part 251 (351).

The opening/closing part 252 (352) is configured to cause, based on the dynamics of an air cylinder 252a (352a), the hand part 251 (351) to open and close so as to hold the sample container 100.

The vertically moving part 253 (353) is configured to move, based on the dynamics of a stepping motor 253a (353a), the hand part 251 (351) along a rail 253b (353b) in the vertical directions (arrow Z directions).

The agitator 254 (354) is configured to move the hand part 251 (351) in the vertical directions (arrow Z directions) in a swinging manner based on the dynamics of a corresponding stepping motor (not shown).

As shown in FIG. 2, the sample container moving part 255 (355) has the sample setting part 255a (355a), and is capable of moving the sample setting part 255a (355a) to predetermined positions in accordance with operations performed during a measurement process. To be specific, the sample container moving part 255 (355) is capable of disposing the corresponding sample setting part in the corresponding aspirating position shown in FIG. 2, and disposing the corresponding sample setting part on a path along which the hand part 251 (351) is moved. The sample container moving part 255 (355) is also configured to hold, in a fixed manner, a sample container 100 in the corresponding aspirating position.

The bar code reader 256 (356) is configured to read a bar code 100a affixed to each sample container 100. The bar code 100a of each sample container 100 is uniquely assigned to the sample therein, and used to manage analysis results of each sample.

Figure 5:
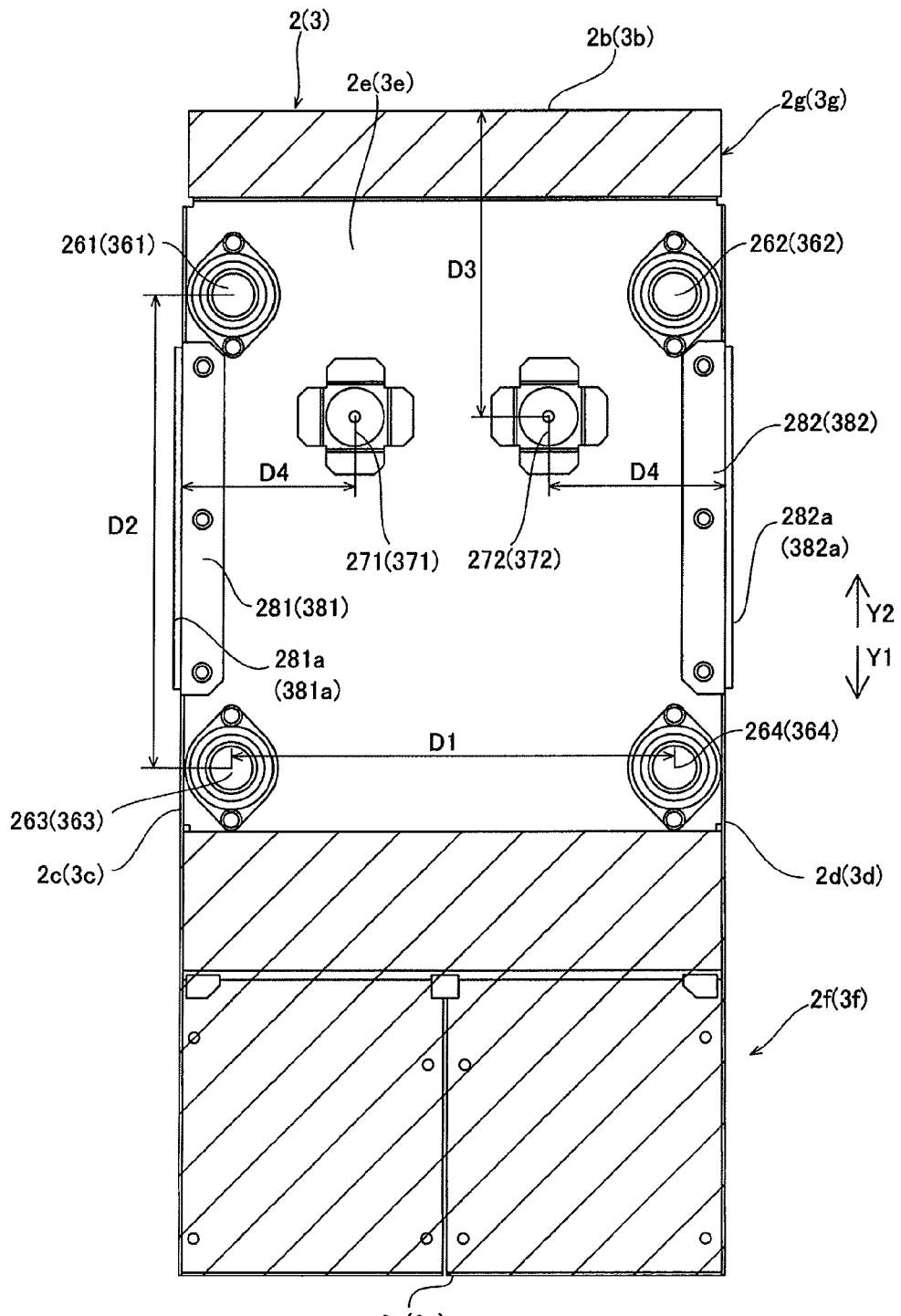
FIG. 5 is a bottom view of the measurement units of the blood analyzer according to the embodiment of the present invention.

As shown in FIG. 5, provided on a bottom face 2e of the first measurement unit 2 are: four ball casters 261, 262, 263, and 264; two inclination restricting members 271 and 272; and two fixing members 281 and 282. Also, provided on a bottom face 3e of the second measurement unit 3 are: four ball casters 361, 362, 363, and 364; two inclination restricting members 371 and 372; and two fixing members 381 and 382. Note that the shapes of, and the component arrangements on, the bottom faces 2e and 3e of the first and second measurement units 2 and 3 are identical to each other.

In the present embodiment, the ball casters 261 to 264 (361 to 364) are provided near the four corners, respectively, of the bottom face 2e (3e) of the measurement unit 2(3). These ball casters 261 to 264 (361 to 364) have a function of smoothing the movement and rotation of the measurement unit 2(3) on the base 6. Further, the ball casters 261 to 264 (361 to 364) are arranged such that the ball caster 263 (363) and the ball caster 264 (364), which are lined up in the X direction and which are adjacent to each other, have an interval D1 therebetween. Similarly, the ball caster 261 (361) and the ball caster 262 (362) have the interval D1 therebetween. Further, the ball caster 261 (361) and the ball caster 263 (363), which are lined up in the Y direction and which are adjacent to each other, have an interval D2 therebetween. Similarly, the ball caster 262 (362) and the ball caster 264 (364) have the interval D2 therebetween. Note that an area within which the first measurement unit 2 and the second measurement unit 3 move is restricted to a predetermined area, as a result of these ball casters 261 to 264 and 361 to 364 coming into contact with below-described first guides 611 and 612 and second guides 621 and 622 which are provided on the base 6.

Figure 6:
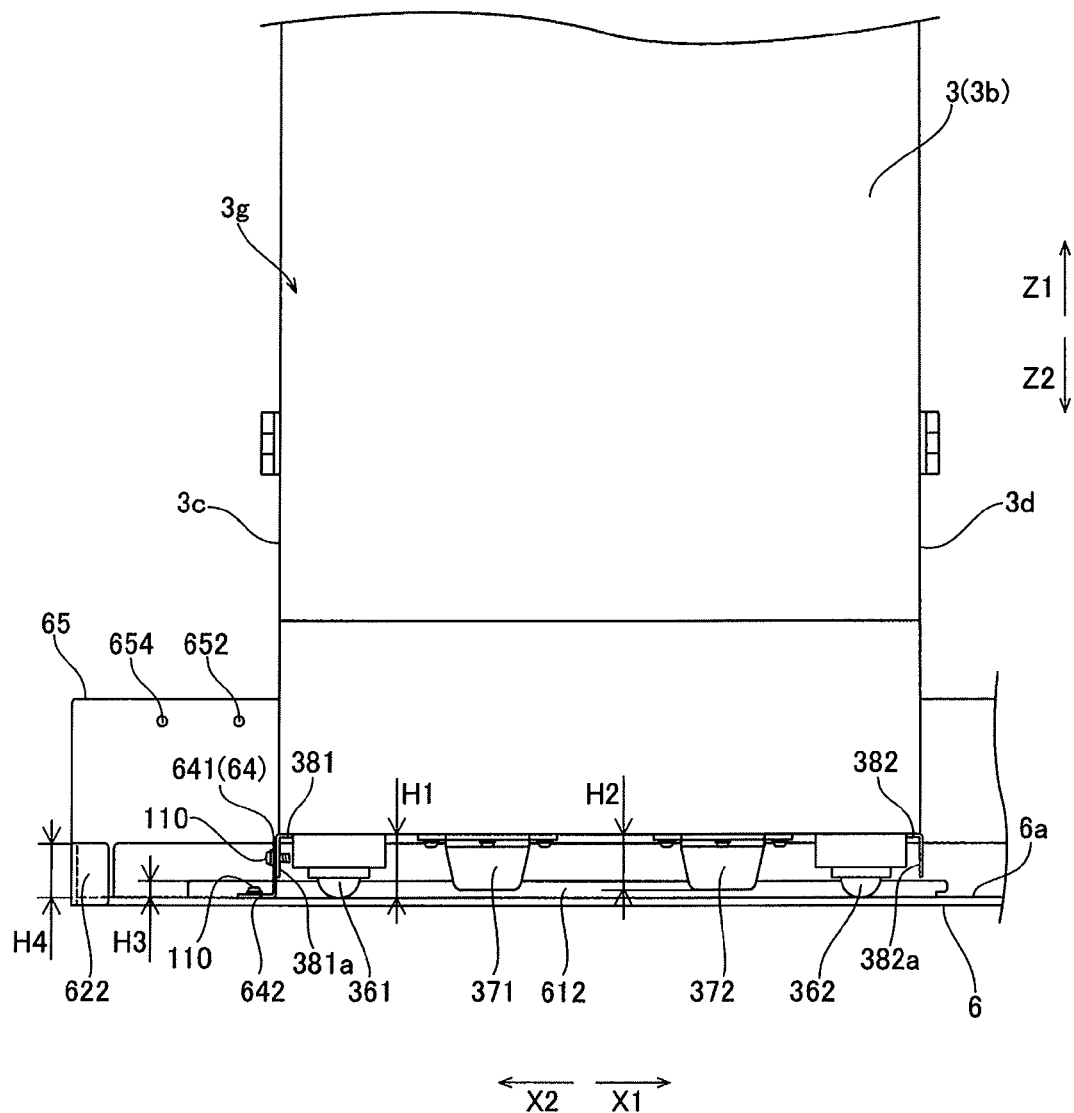
FIG. 6 is a back view of a measurement unit of the blood analyzer according to the embodiment of the present invention.

The two inclination restricting members 271 and 272 (371 and 372) are formed of an elastic material such as rubber, and are provided, on the bottom face 2e (3e) of the measurement unit 2(3), at positions that are both distant from the back face 2b (3b) toward the inside by a distance D3. Further, the inclination restricting member 271 (371) is disposed so as to be distant from the one side face 2c (3c) by a distance D4, and the inclination restricting member 272 (372) is disposed so as to be distant from the other side face 2d (3d) by the distance D4. As shown in FIG. 6, these inclination restricting members 271 and 272 (371 and 372) have a downward projection height H2 that is slightly smaller than a downward projection height H1 of the ball casters 261 to 264 (361 to 364). Accordingly, the inclination restricting members 271 and 272 (371 and 372) are configured so as not to contact a top face 6a of the base 6 when all the four ball casters 261 to 264 (361 to 364) are arranged on the base 6. The inclination restricting members 271 and 272 (371 and 372) are configured to restrict an inclination of the first measurement unit 2 (second measurement unit 3), by coming into contact with the top face 6a of the base 6 when the first measurement unit 2 (second measurement unit 3) becomes inclined with respect to the base 6 due to one of the four ball casters 261 to 264 (361 to 364) being displaced from the base 6.

Figure 7:
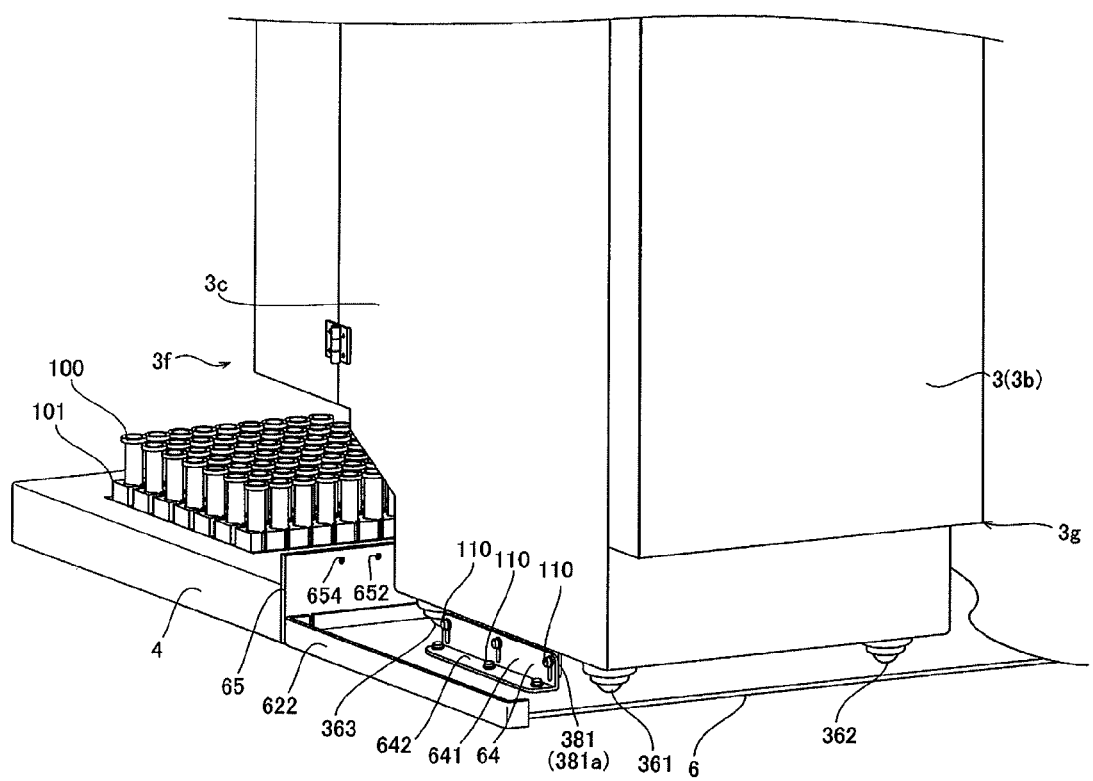
FIG. 7 is a perspective view illustrating the measurement unit of the blood analyzer according to the embodiment of the present invention.

As shown in FIG. 5, the fixing members 281 and 282 (381 and 382) are provided for fixing the first measurement unit 2 (second measurement unit 3) in a below-described first loading position P1 (see FIG. 14) or second loading position P2 (see in FIG. 23) for loading of a sample container 100 containing a sample. As shown in FIG. 6, these fixing members 281 and 282 (381 and 382) are L-shaped, and have fitting portions 281a and 282a (381a and 382a), respectively, which extend downward (in the Z2 direction) along the respective side faces when fixed to the bottom face 2e (3e). As shown in FIG. 7, the fitting portions 281a and 282a (381a and 382a) of the fixing members 281 and 282 (381 and 382) are each provided with screw holes that are not shown, and fastened to a below-described side face fixing member 64 by screws 110. In this manner, each measurement unit is fixed in the loading position on the base 6 (the first loading position P1 or the second loading position P2). Although FIGS. 6 and 7 show that the fixing member 381 (fitting portion 381a) is fastened to the side face fixing member 64 by the screws 110, the other fixing members 281, 282 and 382 are fastened in the same manner. Also, as shown in FIGS. 5 and 6, the fixing member 281 (381) is disposed, on the bottom face 2e (3e), at the one side face 2c (3c) side such that the fitting portion 281a (381a) is practically flush with the one side face 2c (3c). The fixing member 282 (382) is disposed, on the bottom face 2e (3e), at the other side face 2d (3d) side such that the fitting portion 282a (382a) is practically flush with the other side face 2d (3d).

Figure 8:
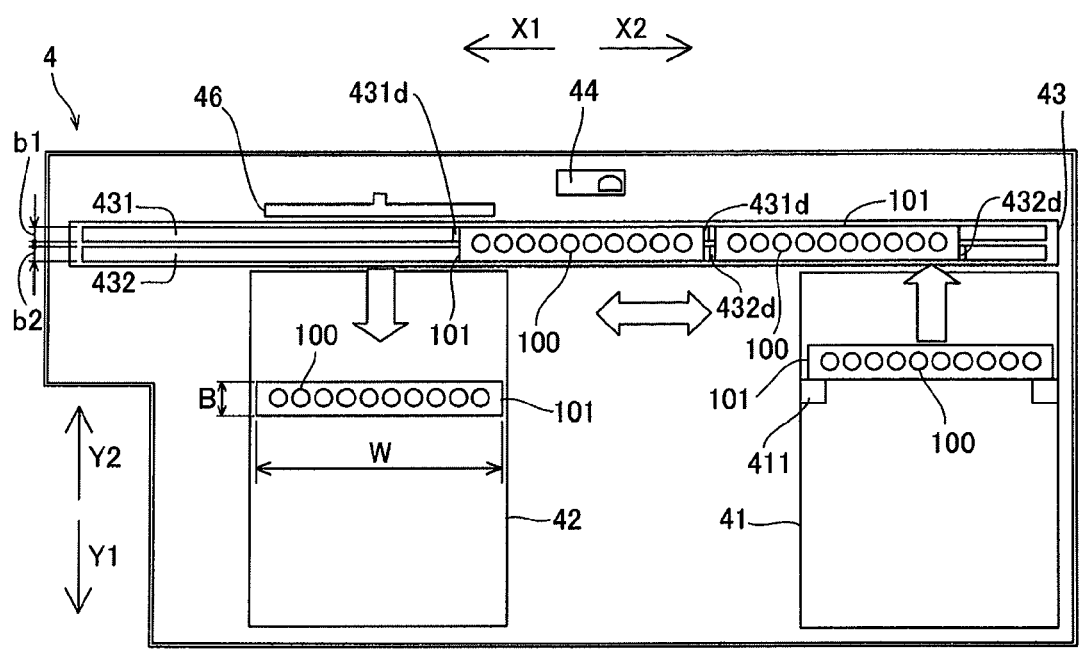
FIG. 8 is a plan view illustrating the sample transporting apparatus of the blood analyzer according to the embodiment of the present invention.

As shown in FIGS. 2, 3 and 8, the sample transporting apparatus 4 includes: an unanalyzed rack holder 41 capable of holding a plurality of racks 101 each accommodating sample containers 100 that contain unanalyzed samples; an analyzed rack holder 42 capable of holding a plurality of racks 101 each accommodating sample containers 100 that contain samples having been analyzed; a rack transporter 43 for horizontally and rectilinearly moving a rack 101 in arrow X directions; a bar code reader 44; a presence/absence detection sensor 45 for detecting presence/absence of a sample container 100 (see FIGS. 2 and 3); and a rack sending out section 46 for moving the rack 101 to the inside of the analyzed rack holder 42.

The unanalyzed rack holder 41 has a rack feeder 411, and is configured such that the racks 101 held by the unanalyzed rack holder 41 are pushed, one by one, onto the rack transporter 43 by the rack feeder 411 moving in the arrow Y2 direction. The rack feeder 411 is configured to be driven by a stepping motor (not shown) provided below the unanalyzed rack holder 41. Further, the unanalyzed rack holder 41 has a restricting portion 412 (see FIG. 3) near the rack transporter 43, and is configured to restrict, by the restricting portion 412, the movement of the racks 101 such that once a rack 101 is pushed onto the rack transporter 43, the rack 101 does not return to the inside of the unanalyzed rack holder 41.

The analyzed rack holder 42 has a restricting portion 421 (see FIG. 3) near the rack transporter 43, and is configured to restrict, by the restricting portion 421, the movement of the racks 101 such that once a rack 101 is moved to the inside of the analyzed rack holder 42, the rack 101 does not return to the rack transporter 43.

Figure 9:
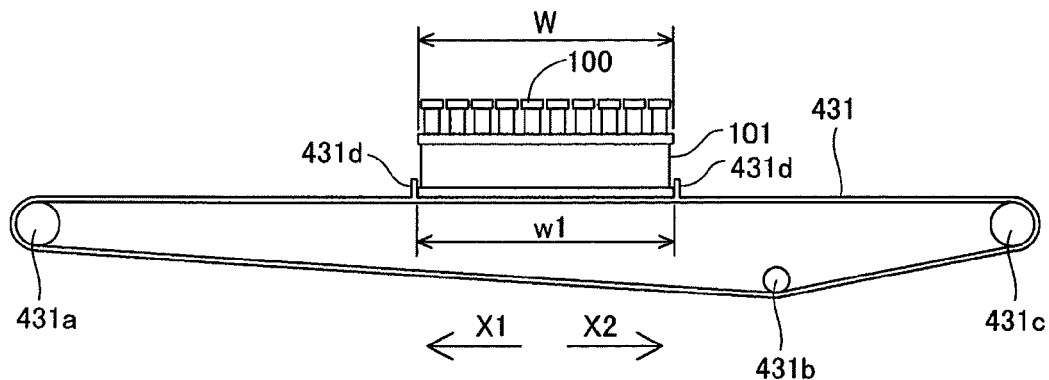
FIG. 9 is a side view illustrating the sample transporting apparatus of the blood analyzer according to the embodiment of the present invention.
Figure 10:
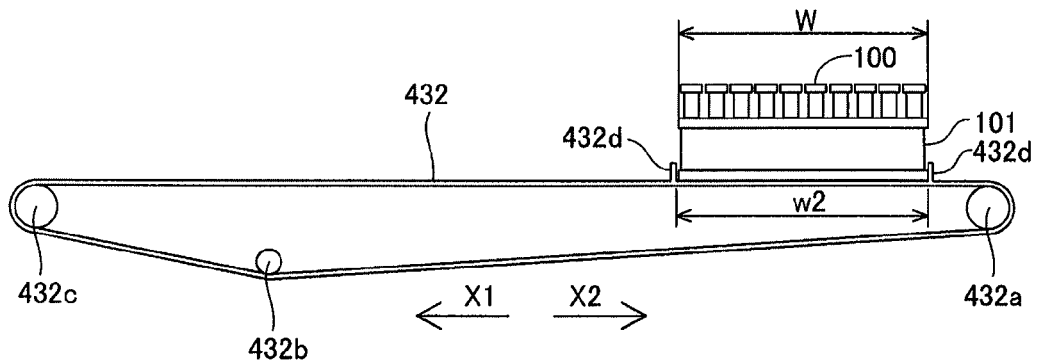
FIG. 10 is a side view illustrating the sample transporting apparatus of the blood analyzer according to the embodiment of the present invention.

As shown in FIG. 8, the rack transporter 43 has two belts that are a first belt 431 and a second belt 432 capable of moving independently of each other. A width b1 of the first belt 431 and a width b2 of the second belt 432 in the arrow Y direction are each equal to or smaller than the half of a width B of the rack 101 in the arrow Y direction. This allows both the first belt 431 and the second belt 432 to be arranged in parallel and not to be displaced from the width B of the rack 101 when the rack transporter 43 transports the rack 101. Further, as shown in FIGS. 9 and 10, the first belt 431 and the second belt 432 are each formed in an annular shape, and are provided so as to be wound around rollers 431a to 431c (see FIG. 9) and rollers 432a to 432c (see FIG. 10), respectively. The outer periphery of the first belt 431 has two protrusions 431d formed thereon and the outer periphery of the second belt 432 has two protrusions 432d formed thereon, such that an interval between the protrusions 431d and an interval between the protrusions 432d have an inner width w1 (see FIG. 9) and an inner width w2 (see FIG. 10), respectively, which are both slightly greater (e.g., by approximately 1 mm) than a width W of the rack 101 in the arrow X direction. The first belt 431 is configured to move, when holding the rack 101 between the protrusions 431d, the rack 101 in an arrow X1 direction or arrow X2 direction as a result of being moved around the rollers 431a to 431c by a stepping motor (not shown). Note that the second belt 432 is configured in the same manner as that of the first belt 431.

Figure 4:
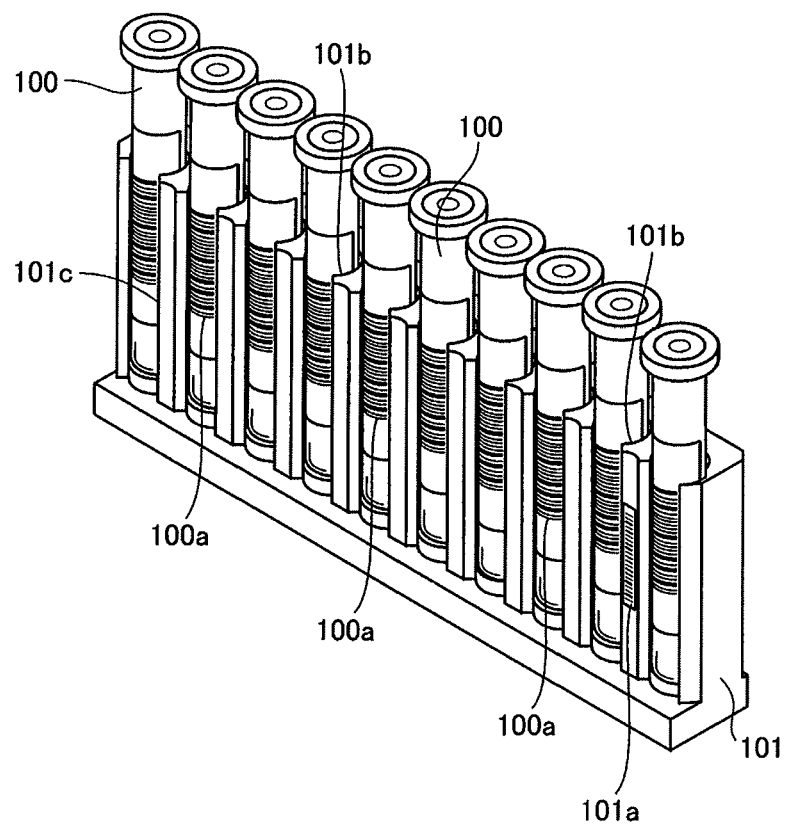
FIG. 4 is a perspective view showing a rack and sample containers of the blood analyzer according to the embodiment of the present invention.

The bar code reader 44 is configured to read the bar code 100a of each sample container 100 shown in FIG. 4 and a bar code 101a affixed to the rack 101. The bar code reader 44 is configured to read the bar code 100a of a target sample container 100 accommodated in the rack 101 when the target sample container 100 is being horizontally rotated by a rotator that is not shown. Accordingly, even in the case where the bar code 100a of the sample container 100 is affixed at the opposite side to the bar code reader 44, the bar code 100a can be caused to face the bar code reader 44 through the rotation of the sample container 100. Note that the bar code 101a is uniquely assigned to each rack 101, and used for, e.g., managing analysis results of the samples.

The presence/absence detection sensor 45 has a curtain-like contact segment 451 (see FIG. 3), a light emitting element for emitting light (not shown), and a light receiving element (not shown). The presence/absence detection sensor 45 is configured such that the contact segment 451 is bent when contacted by a detection subject, and as a result, the light emitted from the light emitting element is reflected by the contact segment 451 and then incident on the light receiving element. Accordingly, when a sample container 100 which is accommodated in the rack 101 and which is a detection subject passes below the presence/absence detection sensor 45, the contact segment 451 is bent by the sample container 100. As a result, the presence of the sample container 100 can be detected.

The rack sending out section 46 is disposed so as to be opposed to the analyzed rack holder 42 while having the rack transporter 43 positioned therebetween, and is configured to horizontally and rectilinearly move in the arrow Y directions. Accordingly, when the rack 101 is transported so as to be positioned between the analyzed rack holder 42 and the rack sending out section 46 (hereinafter, referred to as a rack sending out position), the rack 101 can be pushed to move to the inside of the analyzed rack holder 42 by moving the rack sending out section 46 toward the analyzed rack holder 42 side.

Figure 11:
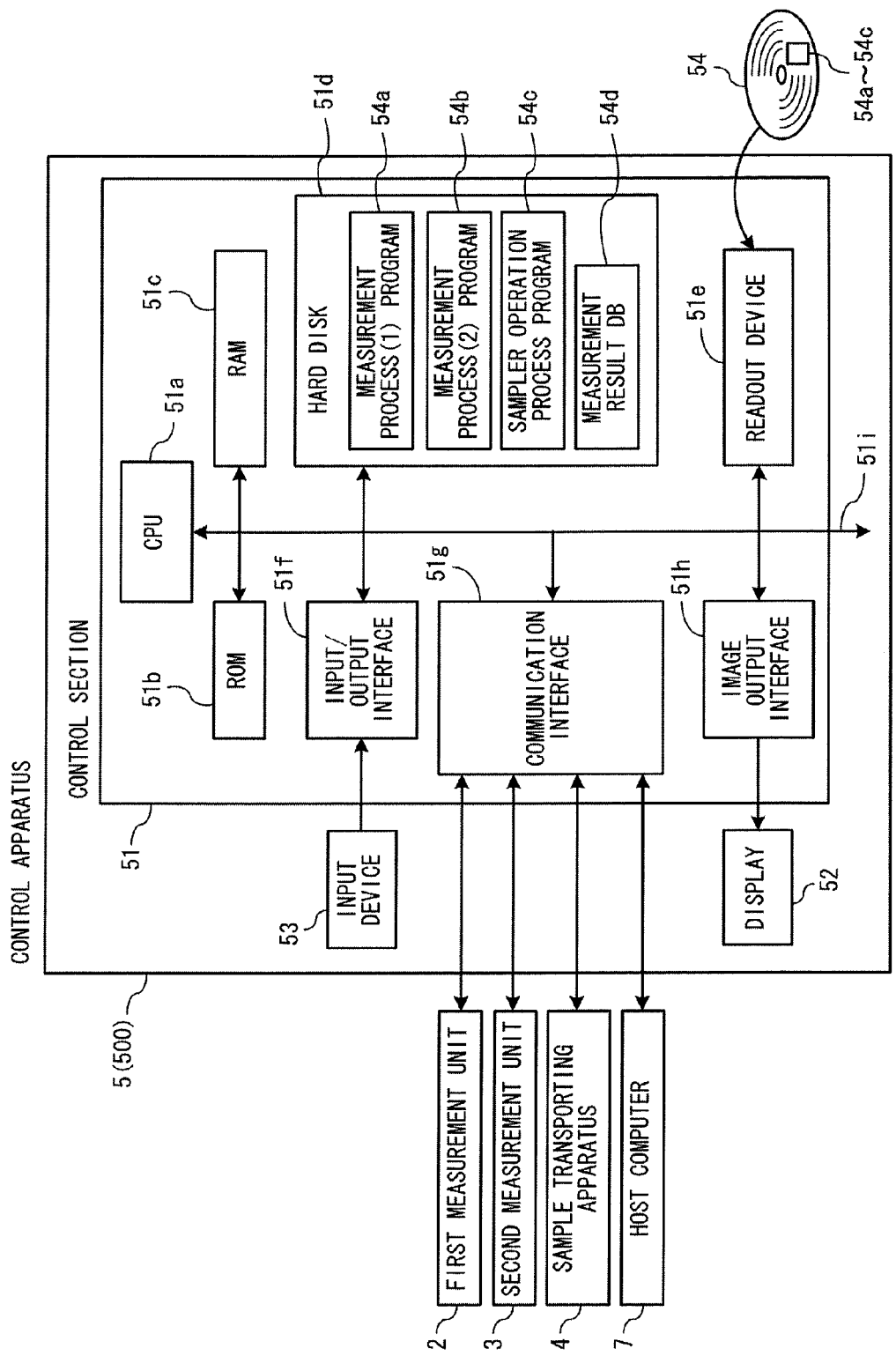
FIG. 11 is a block diagram illustrating a control apparatus of the blood analyzer according to the embodiment of the present invention.

As shown in FIGS. 1, 2 and 11, the control apparatus 5 is structured as a personal computer (PC) or the like. The control apparatus 5 includes: a control section 51 (see FIG. 11) including a CPU, ROM, RAM and the like; a display 52; and an input device 53. The display 52 is provided so as to display analysis results and the like that are obtained by analyzing digital signal data transmitted from the first measurement unit 2 and the second measurement unit 3.

As shown in FIG. 11, the control apparatus 5 is structured as a computer 500 of which the main components are the control section 51, the display 52, and the input device 53. The main components of the control section 51 are a CPU 51a, a ROM 51b, a RAM 51c, a hard disk 51d, a readout device 51e, an input/output interface 51f, a communication interface 51g, and an image output interface 51h. The CPU 51a, ROM 51b, RAM 51c, hard disk 51d, readout device 51e, input/output interface 51f, communication interface 51g, and the image output interface 51h are connected to each other via a bus 51i.

The CPU 51a is capable of executing computer programs stored in the ROM 51b and computer programs loaded into the RAM 51c. The computer 500 acts as the control apparatus 5 through execution, by the CPU 51a, of application programs 54a to 54c that are described below.

The ROM 51b is structured as a mask ROM, PROM, EPROM, EEPROM or the like, and stores computer programs to be executed by the CPU 51a and stores data to be used by the computer programs.

The RAM 51c is structured as an SRAM, DRAM or the like. The RAM 51c is used for reading computer programs stored in the ROM 51b and the hard disk 51d. The RAM 51c is used as a work area for the CPU 51a when the CPU 51a executes these computer programs.

Installed in the hard disk 51d are: various computer programs to be executed by the CPU 51a, such as an operating system and application programs; and data to be used for executing these computer programs. A measurement process (1) program 54a for the first measurement unit 2, a measurement process (2) program 54b for the second measurement unit 3, and a sampler operation process program 54c for the sample transporting apparatus 4 are also installed in the hard disk 51d. Through the execution of these application programs 54a to 54c by the CPU 51a, operations of respective components of the first measurement unit 2, the second measurement unit 3, and the sample transporting apparatus 4 are controlled. Further, a measurement result database 54d is also installed in the hard disk 51d.

The readout device 51e is structured as a flexible disc drive, CD-ROM drive, DVD-ROM drive or the like. The readout device 51e is capable of reading computer programs or data, which are stored in a portable storage medium 54. The portable storage medium 54 stores therein the application programs 54a to 54c. The computer 500 is capable of reading the application programs 54a to 54c from the portable storage medium 54 to install the read application programs 54a to 54c in the hard disk 51d.

Note that the application programs 54a to 54c can be provided to the computer 500 not only via the portable storage medium 54, but also from an external device via a telecommunication line (regardless of whether wired or wireless), which external device is communicably connected to the computer 500 by the telecommunication line. For example, the application programs 54a to 54c are stored in a hard disk of a server computer on the Internet. The computer 500 can access the server computer, and download the application programs 54a to 54c from the server computer to install the application programs 54a to 54c in the hard disk 51d.

Also, an operating system that provides a graphical user interface environment, for example, Windows (registered trademark) manufactured and sold by Microsoft Corporation, is installed in the hard disk 51d. In the description below, it is assumed that the application programs 54a to 54c run on the operating system.

For example, the input/output interface 51f is configured as: a serial interface such as USB, IEEE1394 or RS-232-C; a parallel interface such as SCSI, IDE or IEEE 1284; or an analogue interface including a D/A converter, A/D converter and the like. The input device 53 is connected to the input/output interface 51f. A user can input data to the computer 500 by using the input device 53.

The communication interface 51g is an Ethernet (registered trademark) interface, for example. The computer 500 is capable of transmitting/receiving data to/from the first measurement unit 2, the second measurement unit 3, the sample transporting apparatus 4, and the host computer 7 via the communication interface 51g, using a predetermined communication protocol.

The image output interface 51h is connected to the display 52 that is structured with LCD, CRT or the like. Video signals corresponding to image data, which are supplied from the CPU 51a, are outputted to the display 52. The display 52 is configured to display an image (screen) in accordance with the inputted video signals.

The control section 51 having the above configuration is configured to use measurement results transmitted from the first measurement unit 2 and the second measurement unit 3 to analyze components that are analysis subjects, and obtain results of the analysis (red blood count, platelet count, amount of hemoglobin, white blood count, and the like).

Figure 12:
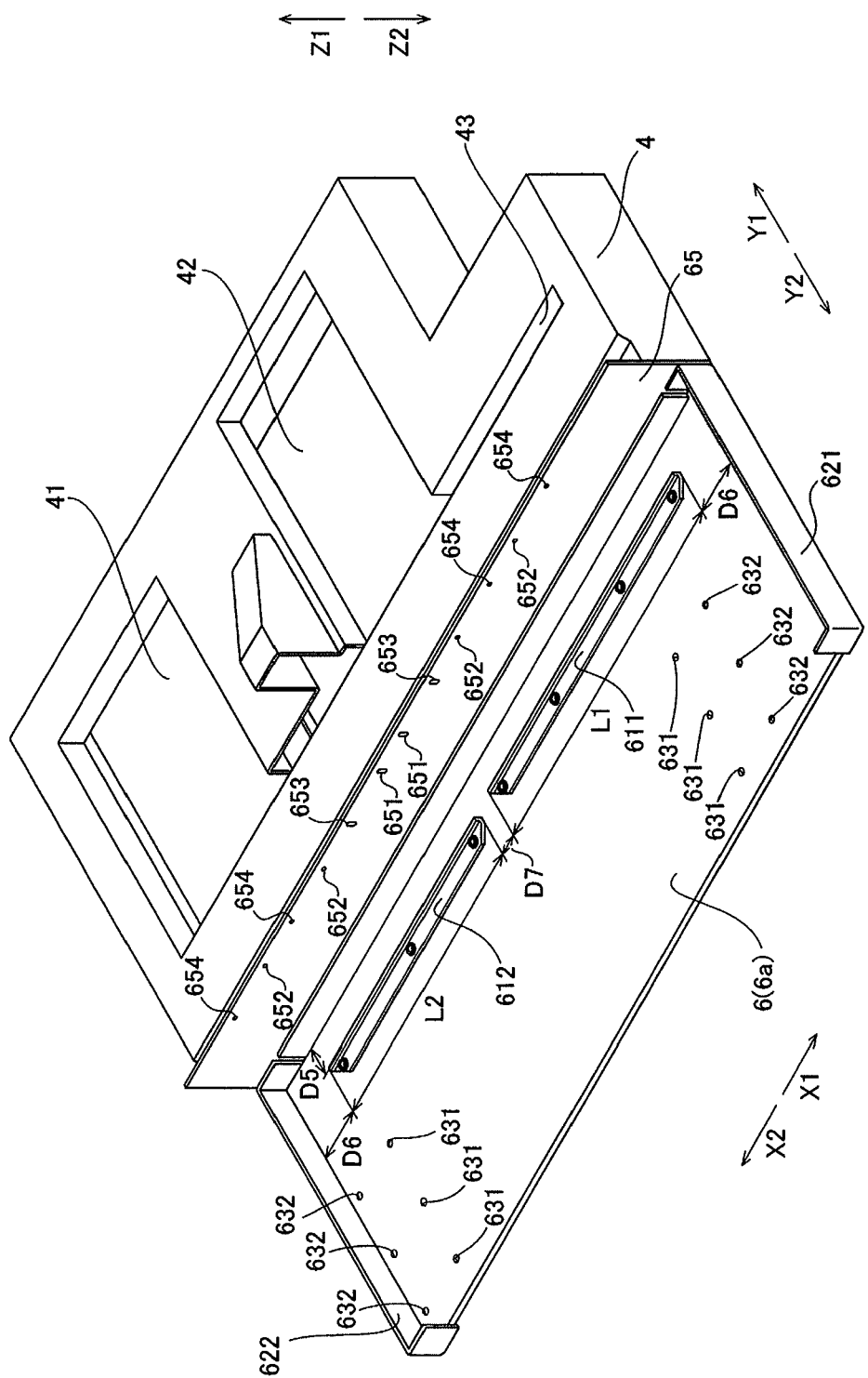
FIG. 12 is a perspective view showing a base of the blood analyzer according to the embodiment of the present invention.

As shown in FIG. 12, the base 6, on which the first measurement unit 2 and the second measurement unit 3 are arranged, has a rectangular shape when viewed in a plan view. The base 6 is provided with a movement restricting sections. The restricting sections restrict, on the base 6, a movement area within which the measurement unit 2(3) moves, wherein the movement restricting sections allow the measurement unit 2(3) to move on the base 6 so as to change orientation of the measurement unit 2(3). The movement restricting sections comprises guides for the first measurement unit and guides for the second measurement unit. The guides for the first measurement unit comprise the first guide 611 and the second guide 621 for restricting movement area of the first measurement apparatus 2 on the base 6. The guides for the second measurement unit comprise first guide 612 and the second guide 622 for restricting the movement area of the second measurement apparatus 3 on the base 6. In order to restrict the movements of these measurement units, the first guides 611 and 612 are each provided for a corresponding one of the measurement units. That is, the first guide 611 is provided corresponding to the first measurement unit 2, and the first guide 612 is provided corresponding to the second measurement unit 3. Formed on the top face 6a of the base 6 are first fixing holes 631 and second fixing holes 632 which are provided for the purpose of fixing each of the first measurement unit 2 and the second measurement unit 3 in the below-described first loading position P1 or second loading position P2. The first fixing holes 631 and the second fixing holes 632 are configured such that the first measurement unit 2 and the second measurement unit 3 can be fixed by the L-shaped side face fixing members 64 (see FIG. 13) at these fixing holes. Further, on the front face side (on the Y1 direction side) of the base 6, a front face fixing member 65 is provided for fixing each measurement unit in the first loading position P1 or in the second loading position P2 that are described below.

The first guides 611 and 612 each have a trapezoidal shape when viewed in a plan view. The first guides 611 and 612 are each provided in a position that is distant, by a distance D5, from the edge of the front face side (Y1 direction side) of the base 6, such that the first guides 611 and 612 extend along the transporting direction (X direction) of the rack 101 (sample containers 100). Further, the first guide 611 disposed on the X1 direction side of the base 6 has a length L1. Whereas, the first guide 612 disposed on the X2 direction side has a length L2 that is shorter than the length L1 of the first guide 611. The length L1 (L2) of the first guide 611 (612) is greater than both the interval D1 and the interval D2 (see FIG. 5), the intervals D1 and D2 each being an interval between two adjacent ball casters among the four ball casters 261 to 264 (361 to 364). The first guide 611 (612) is configured to restrict the range of the movement, on the base 6, of the corresponding measurement unit in the forward/backward directions (Y directions) by being in contact with the ball casters 261 to 264 (361 to 364). Note that as shown in FIG. 6, the first guide 612 has a height H3 that is lower than the height of the bottom face 3e (height H1 of the ball casters) of the second measurement unit 3. Although not shown, the first guide 611 has the same height H3. The first guides 611 and 612 are provided so as to be distant, by intervals D6, from the X direction side edges of the base 6, respectively. Also, the first guide 611 and the first guide 612 are provided so as to be distant from each other by an interval D7. The intervals D6 and D7 both allow each of the ball casters 261 to 264 (361 to 364) to pass therethrough. As a result, the measurement unit 2(3) can be rotated by causing the ball casters 261 to 264 (361 to 364) to pass through the intervals formed at both the ends of the first guide 611 (612).

The second guides 621 and 622 are provided so as to extend along both the side faces of the base 6 on the X direction sides, respectively, the second guides 621 and 622 extending in a direction (Y direction) perpendicular to the transporting direction of the rack 101 (sample containers 100). Accordingly, the second guides 621 and 622 are configured to restrict movement ranges, on the base 6, of the respective measurement units in lateral directions (X directions). The second guides 621 and 622 have bent portions that are fixed along the corners of the base 6. As shown in FIG. 6, the second guide 622 has a height H4 that is greater than the height H3 of the first guide 612. Although not shown, the second guide 621 also has the same height H4 as the second guide 622. Thus, the second guide 621 (622) is configured to prevent, when the corresponding measurement unit is moved, the corresponding measurement unit from falling off the base 6 in the X direction, by being in contact with the ball casters 261 to 264 (361 to 364).

Three first fixing holes 631 are provided in each of two positions on the base 6 for fixing each of the first measurement unit 2 and the second measurement unit 3 in the first loading position P1 by using the side face fixing member 64. Here, the first loading position P1 is a proper position for each measurement unit to be arranged in when the blood analyzer 1 operates normally. The first measurement unit 2 and the second measurement unit 3 are operated concurrently in the first loading position P1 to perform sample measurement processes. Accordingly, the blood analyzer 1 is configured such that the processing efficiency thereof is maximized when the measurement units are each disposed in the first loading position P1.

Figure 14:
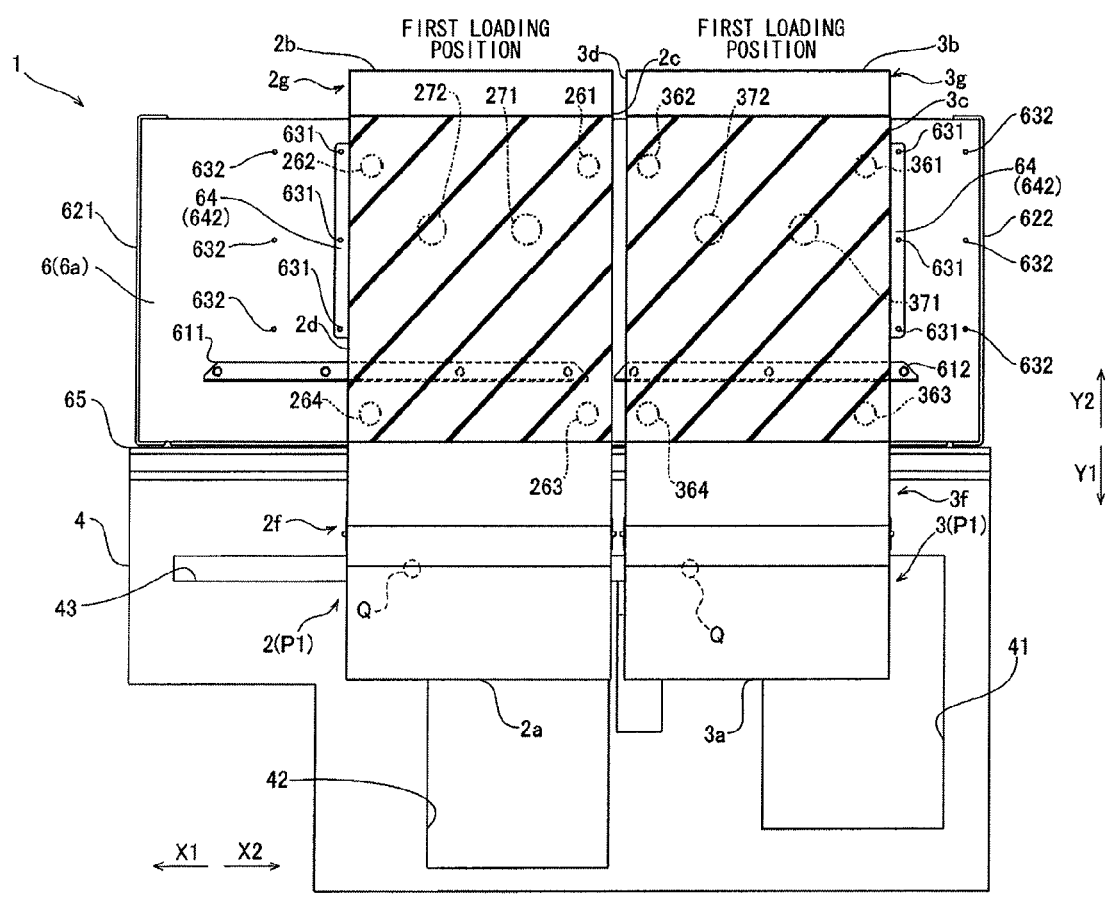
FIG. 14 is a diagram for describing movements, to a maintenance work position and to a second loading position, of the measurement units of the blood analyzer according to the embodiment of the present invention.

The three first fixing holes 631 in each of the two positions are provided such that the side face fixing member 64 (see FIGS. 6 and 7) can be fixed at these holes by screw connection. The first measurement unit 2 disposed on the X1 direction side of the base 6 is fixed in the first loading position P1 by fixing the fixing member 282 on the other side face 2d side to the base 6 via the side face fixing member 64. Further, the second measurement unit 3 disposed on the X2 direction side of the base 6 is fixed in the first loading position P1 by fixing the fixing member 381 on the one side face 3c side to the base 6 via the side face fixing member 64. As shown in FIG. 5, the fixing member 281 and the fixing member 282 (381 and 382) are provided on the one side face side and the other side face side of the corresponding measurement unit, respectively, to be fastened to the side face fixing member 64. Therefore, even if the positions of the first measurement unit 2 and the second measurement unit 3 are switched with each other, each unit can be fixed. Further, as shown in FIG. 14, the first measurement unit 2 is configured such that when the first measurement unit 2 is disposed in the first loading position P1, the two ball casters 263 and 264 that are adjacent to each other on the front side (Y1 direction side) of the first measurement unit 2 are arranged between the first guide 611 and the sample transporting apparatus 4. Similarly, the second measurement unit 3 is configured such that when the second measurement unit 3 is disposed in the first loading position P1, the two ball casters 363 and 364 that are adjacent to each other on the front side (Y1 direction side) of the second measurement unit 3 are arranged between the first guide 612 and the sample transporting apparatus 4.

Figure 21:
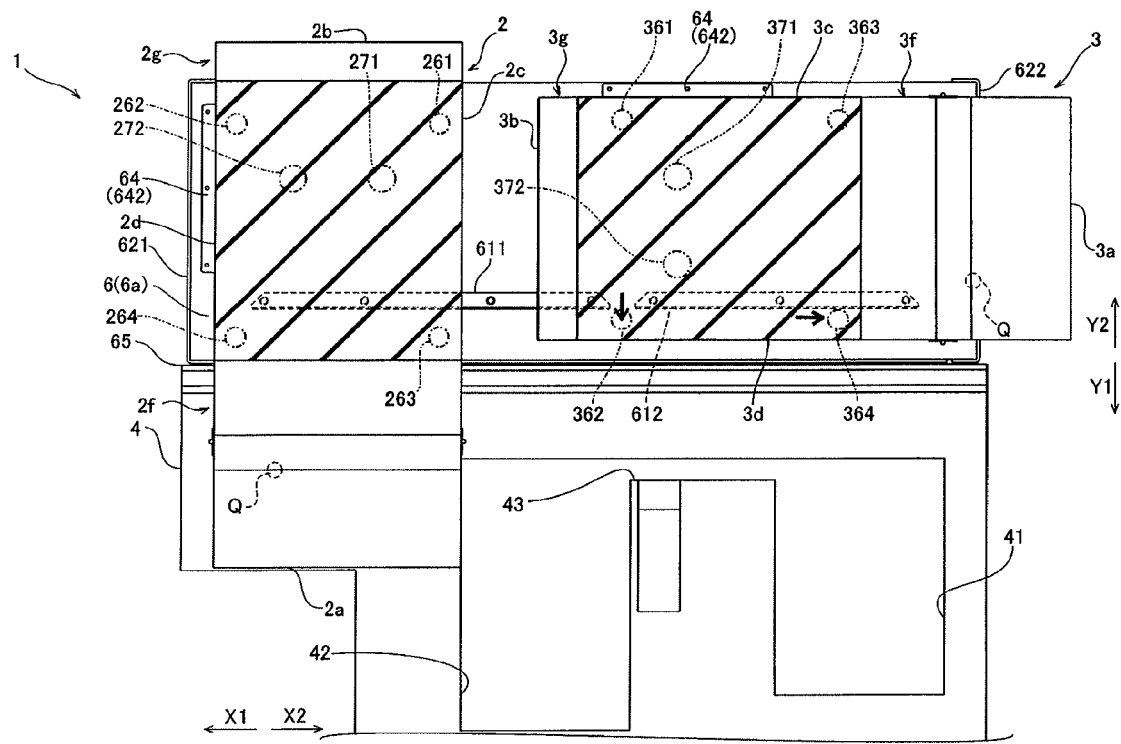
FIG. 21 is a diagram for describing the movements, to the maintenance work position and to the second loading position, of the measurement units of the blood analyzer according to the embodiment of the present invention.
Figure 23:
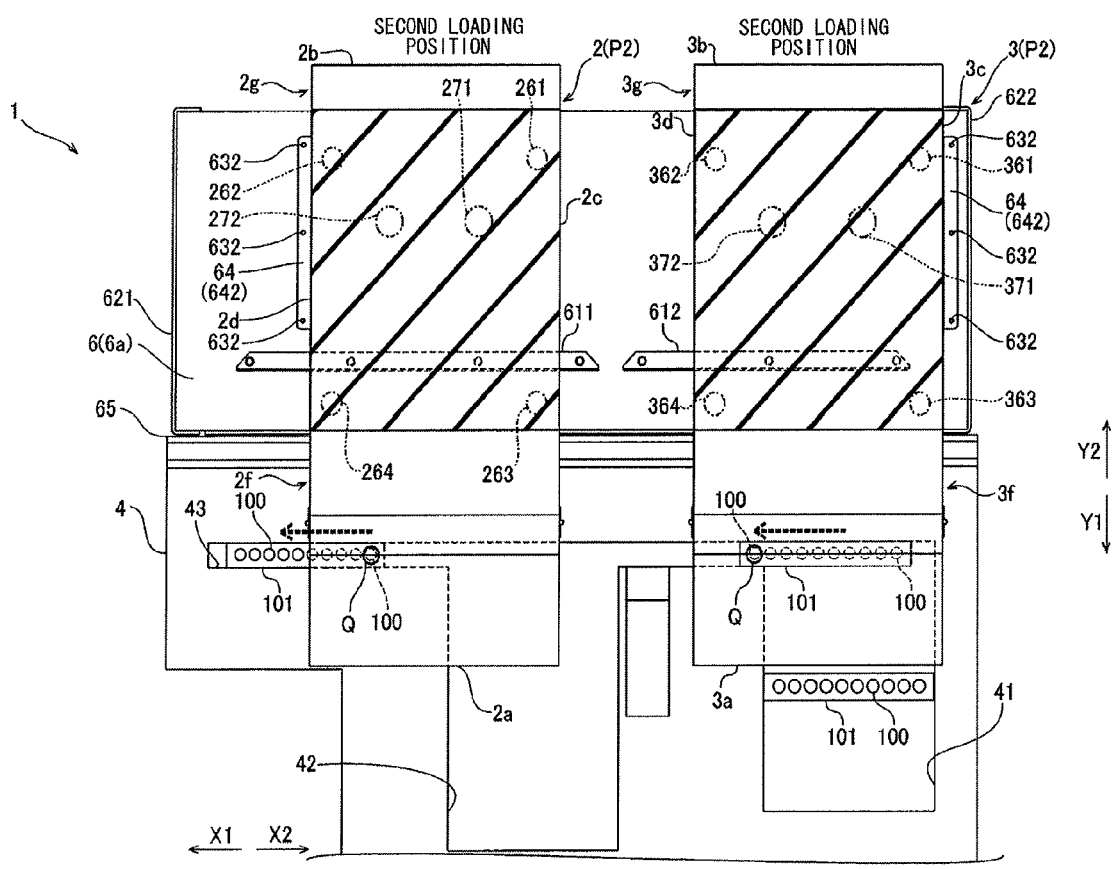
FIG. 23 illustrates a positional relationship of each measurement unit of the blood analyzer according to the embodiment of the present invention, with the rack and the sample containers, each measurement unit being disposed in the second loading position.

Similarly to the first fixing holes 631, three second fixing holes 632 are provided in each of two positions on the base 6 for fixing each of the first measurement unit 2 and the second measurement unit 3 in the second loading position P2 by using the side face fixing member 64. Here, the second loading position P2 is a position in which, when one of the first measurement unit 2 and the second measurement unit 3 is disposed in a maintenance work position for performing a maintenance work of the blood analyzer 1, the other measurement unit continues to perform sample measurement without interfering with the measurement unit on which the maintenance work is being performed. For example, as shown in FIG. 21, when it is necessary to perform maintenance work on the other side face 3d side of the second measurement unit 3 and the second measurement unit 3 is rotated by approximately 90 degrees to dispose the other side face 3d on the front side (Y1 direction side), the first measurement unit 2 needs to be moved from the first loading position P1 in the X1 direction to avoid interference with the second measurement unit 3. The second loading position P2 allows all the sample containers 100 (ten containers in the present embodiment) accommodated in the rack 101 to be loaded into the first measurement unit 2 even when the other side face 3d of the second measurement unit 3 is disposed on the front side (Y1 direction side) for the maintenance work as shown herein. Similarly, in the case where the maintenance work is performed on the first measurement unit 2, the second loading position P2 allows all the sample containers 100 (ten containers in the present embodiment) accommodated in the rack 101 to be loaded into the second measurement unit 3 even when the one side face 2c of the first measurement unit 2 is disposed on the front side (Y1 direction side). As shown in FIG. 23, the first measurement unit 2 is configured such that when the first measurement unit 2 is disposed in the second loading position P2, the two ball casters 263 and 264 that are adjacent to each other on the front side (Y1 direction side) of the first measurement unit 2 are arranged between the first guide 611 and the sample transporting apparatus 4. Similarly, the second measurement unit 3 is configured such that when the second measurement unit 3 is disposed in the second loading position P2, the two ball casters 363 and 364 that are adjacent to each other on the front side (Y1 direction side) of the second measurement unit 3 are arranged between the first guide 612 and the sample transporting apparatus 4. The movement of each measurement unit at the time of maintenance work will be described later in detail.

The three second fixing holes 632 in each of the two positions are provided such that the side face fixing member 64 can be fixed at these holes by screw connection. The first measurement unit 2 disposed on the X1 direction side of the base 6 is fixed in the second loading position P2 by fixing the fixing member 282 on the other side face 2d side to the base 6 via the side face fixing member 64. Further, the second measurement unit 3 disposed on the X2 direction side of the base 6 is fixed in the second loading position P2 by fixing the fixing member 381 on the one side face 3c side to the base 6 via the side face fixing member 64.

Figure 13:
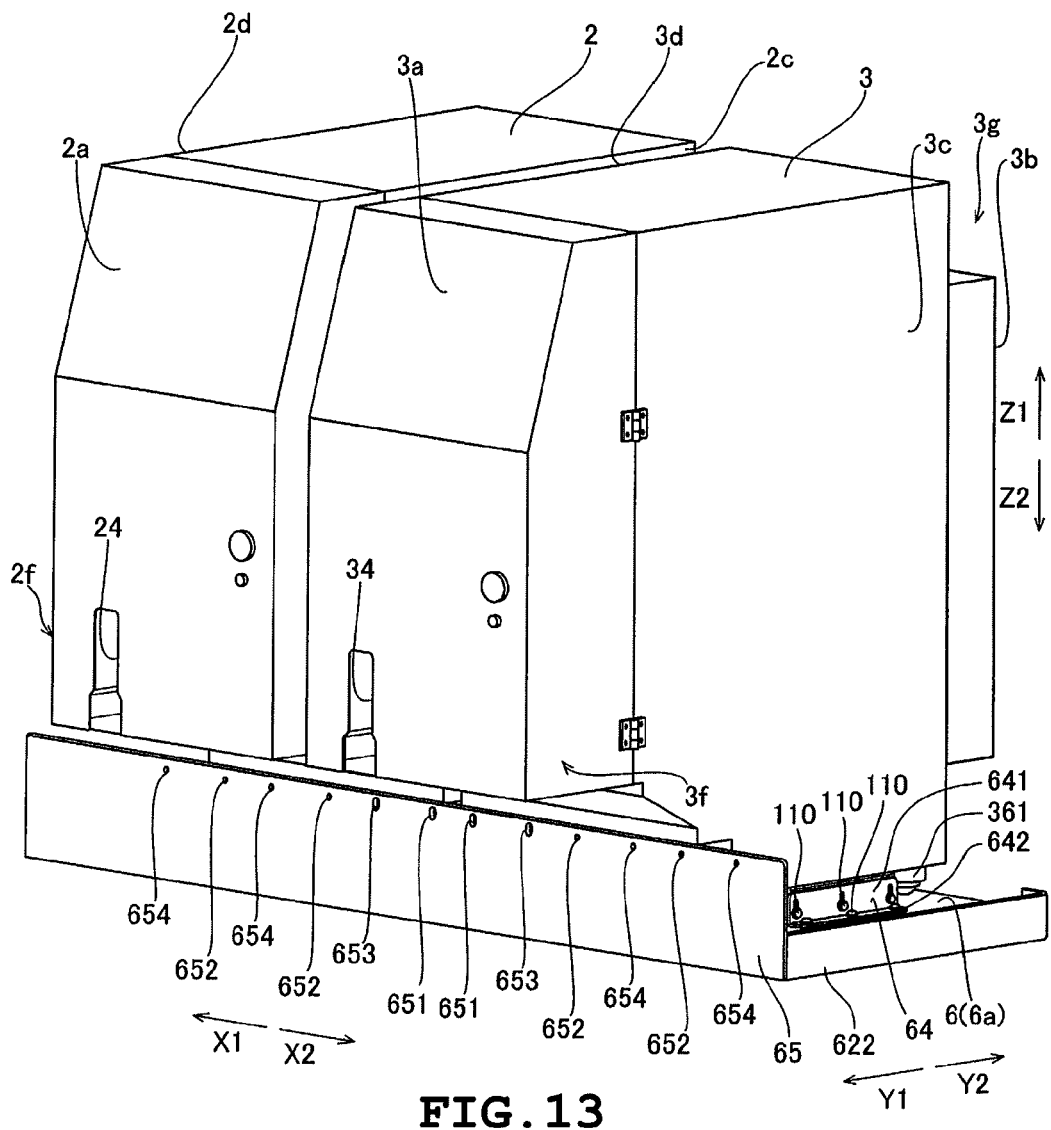
FIG. 13 is a perspective view illustrating the base of the blood analyzer according to the embodiment of the present invention.

As shown in FIGS. 6 and 13, the side face fixing member 64 is an L-shaped plate and includes a unit side fitting portion 641 and a base side fitting portion 642. The unit side fitting portion 641 of the side face fixing member 64 is configured to be fastened, by the screws 110, to the fixing member 281 or 282 (381 or 382) provided on the bottom face 2e (3e) of the measurement unit 2(3). Also, the base side fitting portion 642 is configured to be fixed by screw connection at the first fixing holes 631 or the second fixing holes 632 provided in the top face 6a of the base 6. Each measurement unit is configured such that one of the side face sides thereof is fixed to the base 6 via the side face fixing member 64.

As shown in FIGS. 12 and 13, the front face fixing member 65 is a rectangular-shaped plate. The front face fixing member 65 is fitted to the front face of the base 6 (i.e., to the surface on the Y1 direction side). Further, the front face fixing member 65 is provided with first positioning holes 651, first fixing holes 652, second positioning holes 653, and second fixing holes 654. The front face fixing member 65 has functions of positioning each measurement unit in the first loading position P1 or in the second loading position P2, and fixing the front face side of each measurement unit to the base 6.

The first positioning holes 651 are elongate holes that are provided in two positions on the front face fixing member 65. These first positioning holes 651 are provided for positioning the respective measurement units at the time when the measurement units are each fixed in the first loading position P1. To be specific, a protrusion (not shown) provided in a predetermined position on the front face 2a (3a) of the measurement unit 2(3) is inserted into a corresponding one of the first positioning holes 651. In this manner, positioning of each measurement unit is performed. Note that the protrusion that is not shown is formed as a hexagon socket head cap screw that is removable from each measurement unit. Accordingly, the first positioning holes 651 are formed in the two positions as the first positioning hole 651 for positioning the first measurement unit 2 in the first loading position P1 on the X1 direction side of the base 6, and as the first positioning hole 651 for positioning the second measurement unit 3 in the first loading position P1 on the X2 direction side of the base 6. These first positioning holes 651 are provided in positions corresponding to the first fixing holes 631 in the base 6. The measurement unit 2(3) is configured such that when the protrusion thereof is inserted into the corresponding first positioning hole 651, the fixing member provided on the bottom face 2e (3e) can be fixed at the first fixing holes 631 by screw connection by fitting the side face fixing member 64 between the fixing member and the first fixing holes 631.

The first fixing holes 652 are screw holes formed in two positions that correspond to one of the two first positioning holes 651 and screw holes formed in two positions that correspond to the other first positioning hole 651. These first fixing holes 652 are provided for fixing, together with the first fixing holes 631 provided in the top face 6a of the base 6, the measurement units in the first loading position P1. The measurement units are configured to be fixed, when the protrusions thereof are inserted into the first positioning holes 651, by screws that are screwed from the front face side (Y1 direction side) through the first fixing holes 652 into screw holes (not shown) provided in the front faces 2a and 3a of the measurement units. Accordingly, in the first loading position P1, one of the side face sides (one of the X direction sides) of each measurement unit is fixed by screw connection at the first fixing holes 631 of the base 6, and also, the front face side (Y1 direction side) of each measurement unit is fixed by screw connection at the first fixing holes 652 of the front face fixing member 65.

Similarly to the first positioning holes 651, the second positioning holes 653 are elongate holes that are provided in two positions on the front face fixing member 65. These second positioning holes 653 are provided for positioning the respective measurement units at the time when the measurement units are each fixed in the second loading position P2. The protrusion (hexagon socket head cap screw) provided in a predetermined position on the front face 2a (3a) of the measurement unit 2(3) is inserted into a corresponding one of the second positioning holes 653. In this manner, positioning of each measurement unit is performed. The measurement unit 2(3) is configured such that when the protrusion thereof is inserted into the corresponding second positioning hole 653, the fixing member provided on the bottom face 2e (3e) can be fixed at the second fixing holes 632 by screw connection by fitting the side face fixing member 64 between the fixing member and the second fixing holes 632.

The second fixing holes 654 are screw holes formed in two positions that correspond to one of the two second positioning holes 653 and screw holes formed in two positions that correspond to the other second positioning hole 653. These second fixing holes 654 are provided for fixing, together with the second fixing holes 632 provided in the top face 6a of the base 6, the measurement units in the second loading position P2. The measurement units are configured to be fixed, when the protrusions (hexagon socket head cap screws) thereof are inserted into the second positioning holes 653, by screws that are screwed from the front face side (Y1 direction side) through the second fixing holes 654 into screw holes (not shown) provided in the front faces 2a and 3a of the measurement units. Accordingly, in the second loading position P2, one of the side face sides (one of the X direction sides) of each measurement unit is fixed by screw connection at the second fixing holes 632, and also, the front face side (Y1 direction side) of each measurement unit is fixed by screw connection at the second fixing holes 654 of the front face fixing member 65.

As shown in FIG. 4, in the rack 101, ten container accommodating portions 101b are formed so as to be able to accommodate ten sample containers 100 in line. Further, the container accommodating portions 101b are each provided with an opening 101c such that the bar code 100a of each sample container 100 accommodated therein can be visually recognized.

FIGS. 14 to 23 are plan views illustrating movements of the respective measurement units on the base of the blood analyzer according to the embodiment of the present invention. Described next with reference to FIGS. 14 to 23 are movements of the first measurement unit 2 and the second measurement unit 3 at the time when maintenance work is performed on the blood analyzer 1 according to the present embodiment. Note that in FIGS. 14 to 23, the bottom faces 2e and 3e of the respective measurement units are indicated as hatched areas.

At the time of maintenance work, the measurement unit that is a subject of the maintenance work is moved to a position that facilitates the maintenance work (maintenance work position). This maintenance work position varies depending on which part of the measurement unit is subjected to the maintenance work. Accordingly, at the time of maintenance work, the position and orientation of the measurement unit are changed such that the measurement unit is disposed in the maintenance work position that corresponds to the position of a part of the measurement unit, the part being subjected to the maintenance work. In the present embodiment, since the measurement unit 2(3) is configured to be able to move on the base 6 by using the ball casters 261 to 264 (361 to 364), the position and orientation of each measurement unit can be readily changed in accordance with the maintenance work position, and then the maintenance work is performed, accordingly. Note that the blood analyzer 1 includes two measurement units. Therefore, even if the maintenance work is performed on one of the measurement units, the measurement of the samples can be continued by the other measurement unit. Described here is a case where the maintenance work is performed on the second measurement unit 3 disposed on the X2 direction side of the base 6.

The steps of moving the second measurement unit 3 to the maintenance work position vary depending on whether or not there is a necessity to shift the position of the first measurement unit 2, which continues the measurement, from the first loading position P1 (proper position). If the maintenance work is to be performed near the front face 3a of the second measurement unit 3, the maintenance work can be performed without moving the first measurement unit 2 from the first loading position P1.

In this case, as shown in FIG. 14, the second measurement unit 3 that is the subject of the maintenance work is moved from a state where each measurement unit is disposed in the first loading position P1. First, an operator who performs the maintenance work releases the fixedness of the second measurement unit 3 to the base 6. To be specific, the screws 110 for fixing the front face fixing member 65 and the side face fixing member 64 of the second measurement unit 3 are unscrewed to release the fixedness. At this point, the first measurement unit 2 is still fixed in the first loading position P1, and is able to perform the measurement of the samples.

Figure 15:
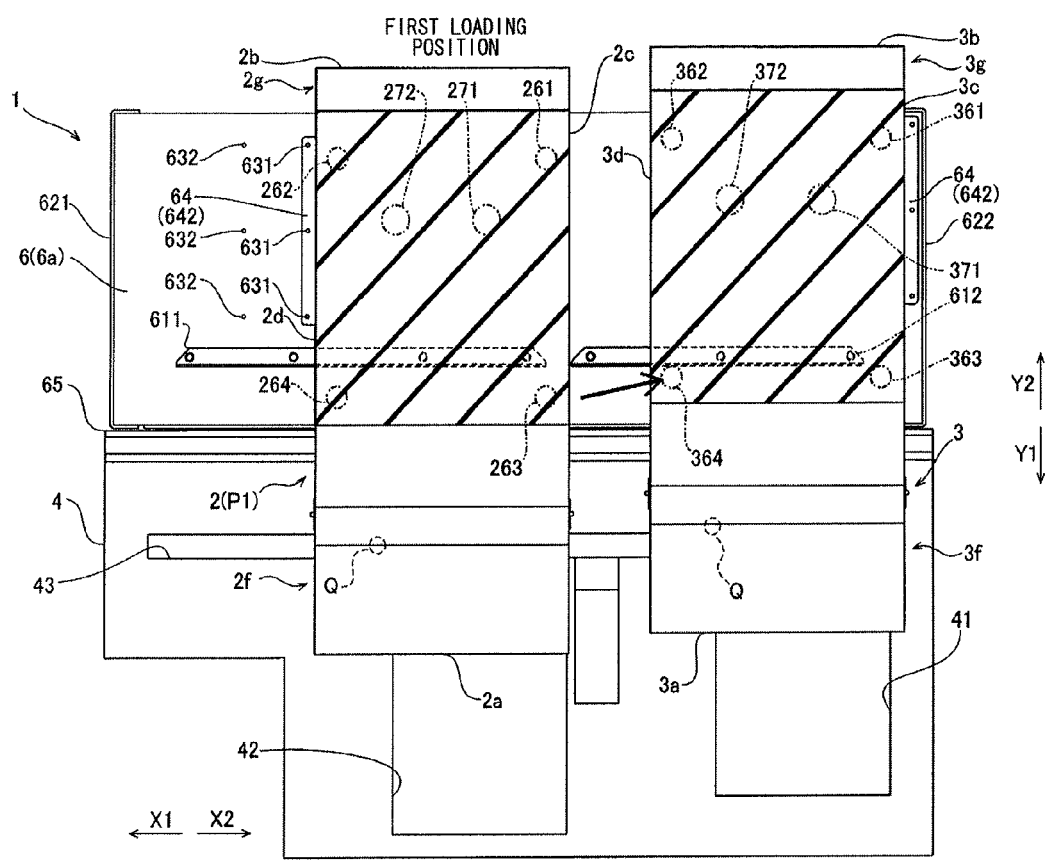
FIG. 15 is a diagram for describing the movements, to the maintenance work position and to the second loading position, of the measurement units of the blood analyzer according to the embodiment of the present invention.

Then, as shown in FIG. 15, the second measurement unit 3 is moved on the base 6 from the first loading position P1 in the X2 direction so as to be positioned near the edge of the X2 direction side of the base 6. At the same time, the second measurement unit 3 is moved backward (in the Y2 direction) until the first guide 612 comes into contact with the ball caster 364. In this manner, the movement of the second measurement unit 3 in the Y2 direction is restricted by the first guide 612.

Figure 16:
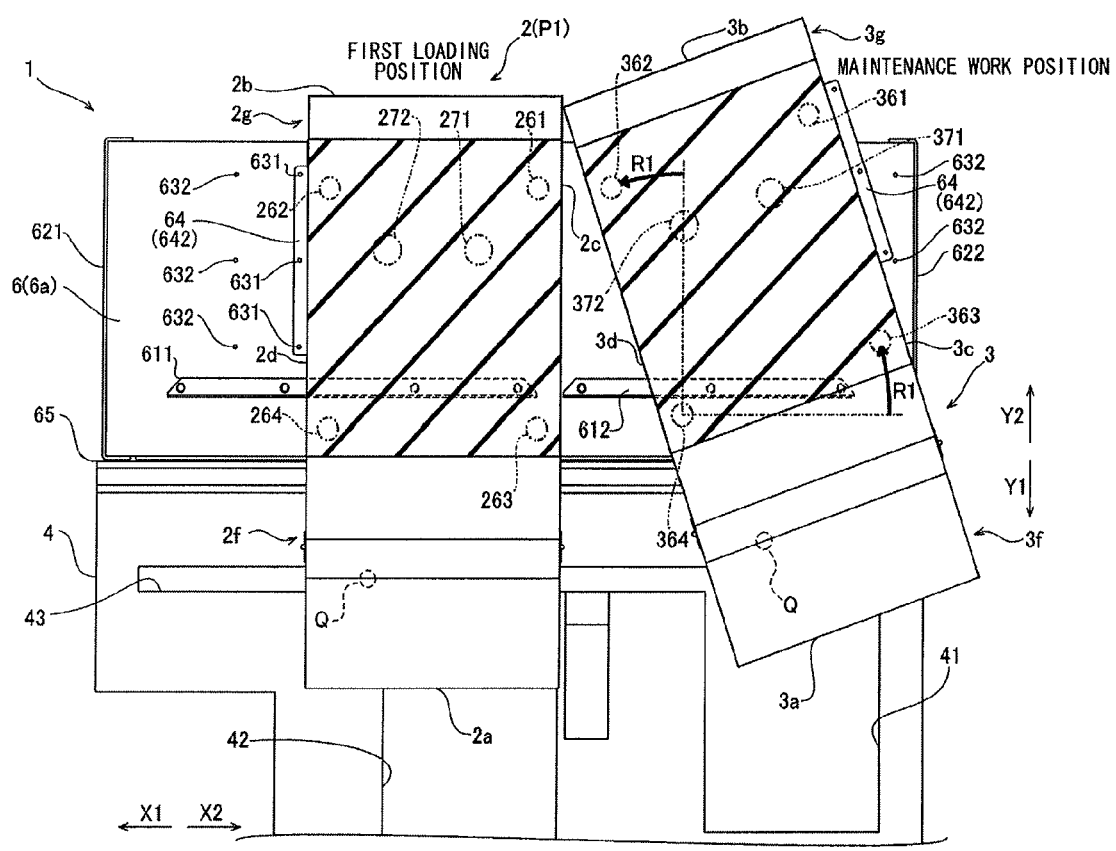
FIG. 16 is a diagram for describing the movements, to the maintenance work position and to the second loading position, of the measurement units of the blood analyzer according to the embodiment of the present invention.

Next, as shown in FIG. 16, the second measurement unit 3 is rotated in an R1 direction with respect to the ball caster 364. In this manner, the second measurement unit 3 is rotated until the corner of the back face 3b interferes with the first measurement unit 2. Thus, the second measurement unit 3 can be moved and rotated to be disposed in the maintenance work position while the first measurement unit 2 remains in the first loading position P1.

In the state shown in FIG. 16, for example, the operator is able to readily access, from the front side (Y1 direction side), a part of the other side face 3d of the second measurement unit 3 near the front face 3a, on which part the maintenance work is to be performed. Further, the first measurement unit 2, on which the maintenance work is not performed, is able to continue the sample measurement process without being moved from the first loading position P1.

On the other hand, in the case where the maintenance work is performed on the other side face 3d of the second measurement unit 3 near the back side (Y2 direction side), the second measurement unit 3 is rotated to be in such a maintenance work position that the other side face 3d is positioned on the front side (Y1 direction side), and then the maintenance work is performed. In this case, since the first measurement unit 2 in the first loading position P1 interferes with the second measurement unit 3, the first measurement unit 2 is needed to be moved to the second loading position P2.

Figure 17:
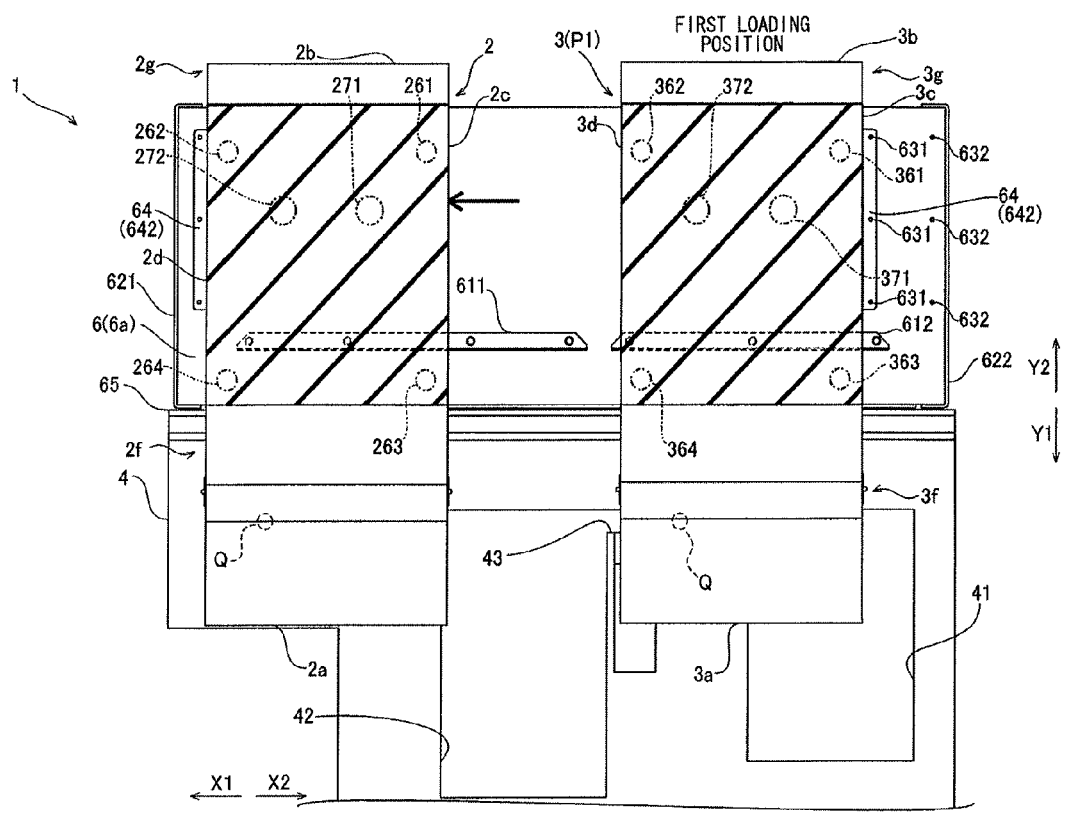
FIG. 17 is a diagram for describing the movements, to the maintenance work position and to the second loading position, of the measurement units of the blood analyzer according to the embodiment of the present invention.

First, as shown in FIG. 17, the operator releases the fixedness of the first measurement unit 2 to the base 6. To be specific, the screws 110 in the front face fixing member 65 and the side face fixing member 64 for fixing the first measurement unit 2 are unscrewed to release the fixedness. As a result, the first measurement unit 2 becomes movable on the base 6. Next, by moving the first measurement unit 2 to the edge of the X1 direction side of the base 6, a space for the second measurement unit 3 to move is obtained.

Figure 18:
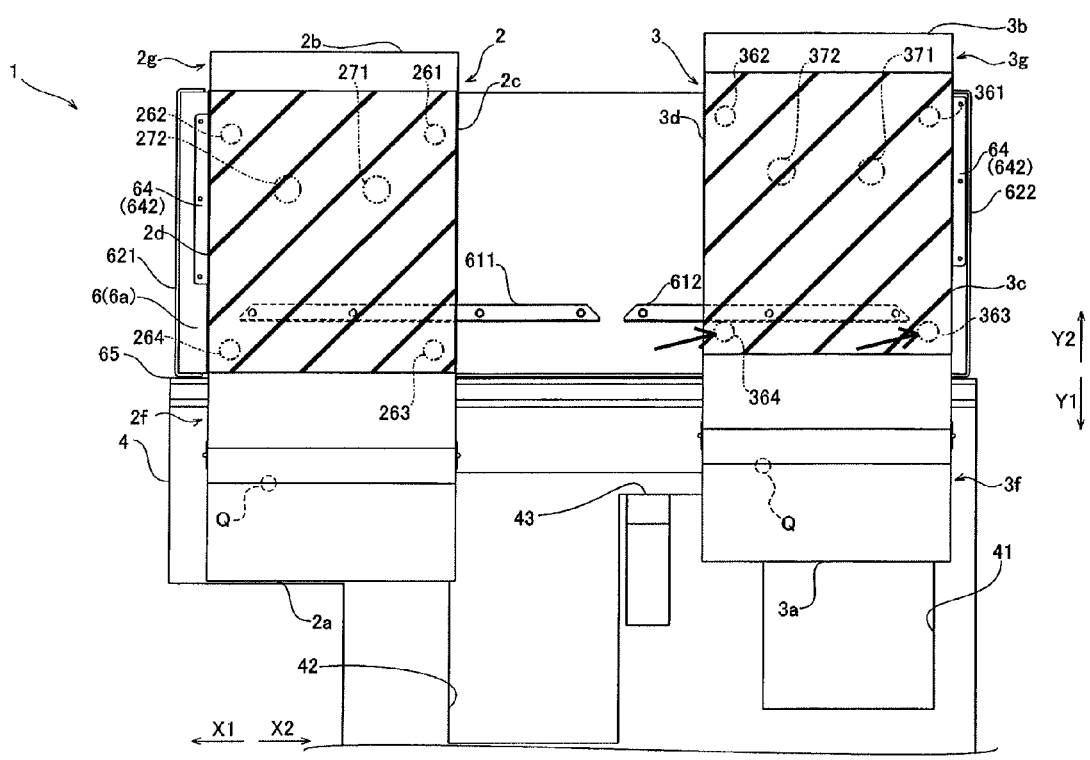
FIG. 18 is a diagram for describing the movements, to the maintenance work position and to the second loading position, of the measurement units of the blood analyzer according to the embodiment of the present invention.

Next, the screws 110 in the front face fixing member 65 and the side face fixing member 64 for fixing the second measurement unit 3 are unscrewed to release the fixedness to the base 6. Thereafter, as shown in FIG. 18, the second measurement unit 3 is moved in the X2 direction to be positioned near the edge of the X2 direction side of the base 6. At the same time, the second measurement unit 3 is moved backward (in the Y2 direction) until the first guide 612 comes into contact with the ball caster 364. In this manner, the movement of the second measurement unit 3 in the Y2 direction is restricted by the first guide 612.

Figure 19:
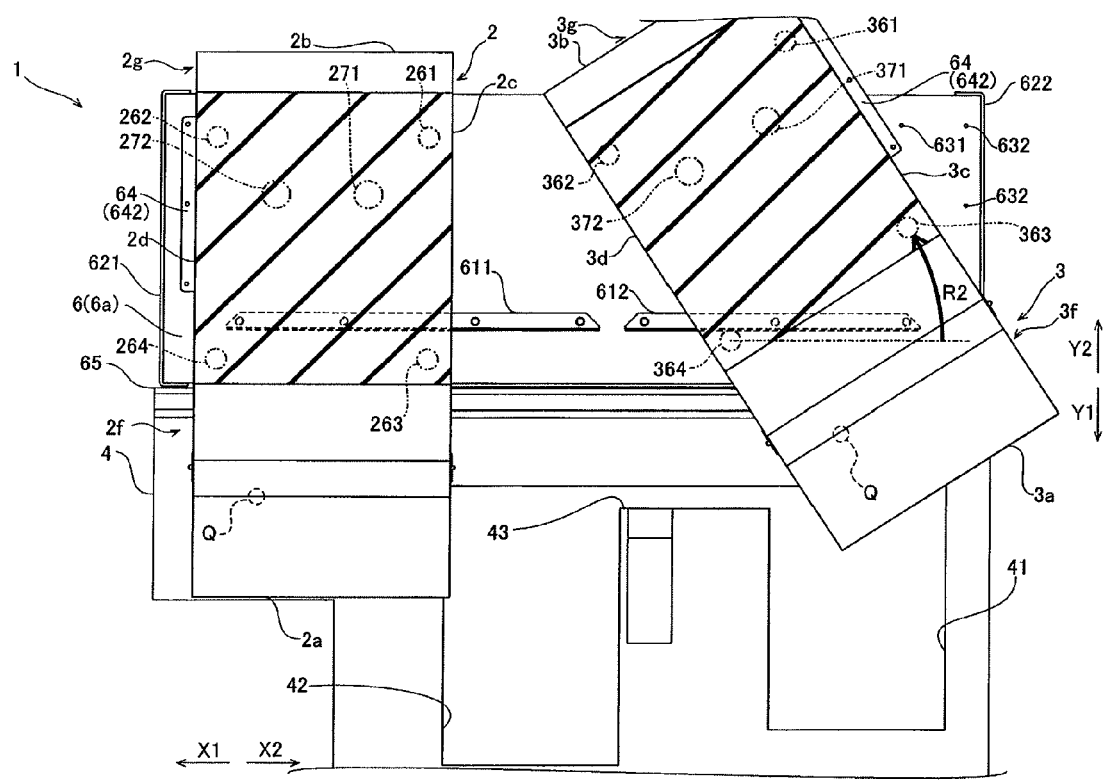
FIG. 19 is a diagram for describing the movements, to the maintenance work position and to the second loading position, of the measurement units of the blood analyzer according to the embodiment of the present invention.

Subsequently, as shown in FIG. 19, the second measurement unit 3 is rotated in an R2 direction with respect to the ball caster 364. In this manner, the ball caster 363 on the front side (Y1 direction side) of the second measurement unit 3 passes by the first guide 612 through the interval on the X2 direction side and moves backward (in the Y2 direction) from the first guide 612. Here, the ball caster 361 is positioned to be displaced backward (in the Y2 direction) from the base 6.

Figure 20:
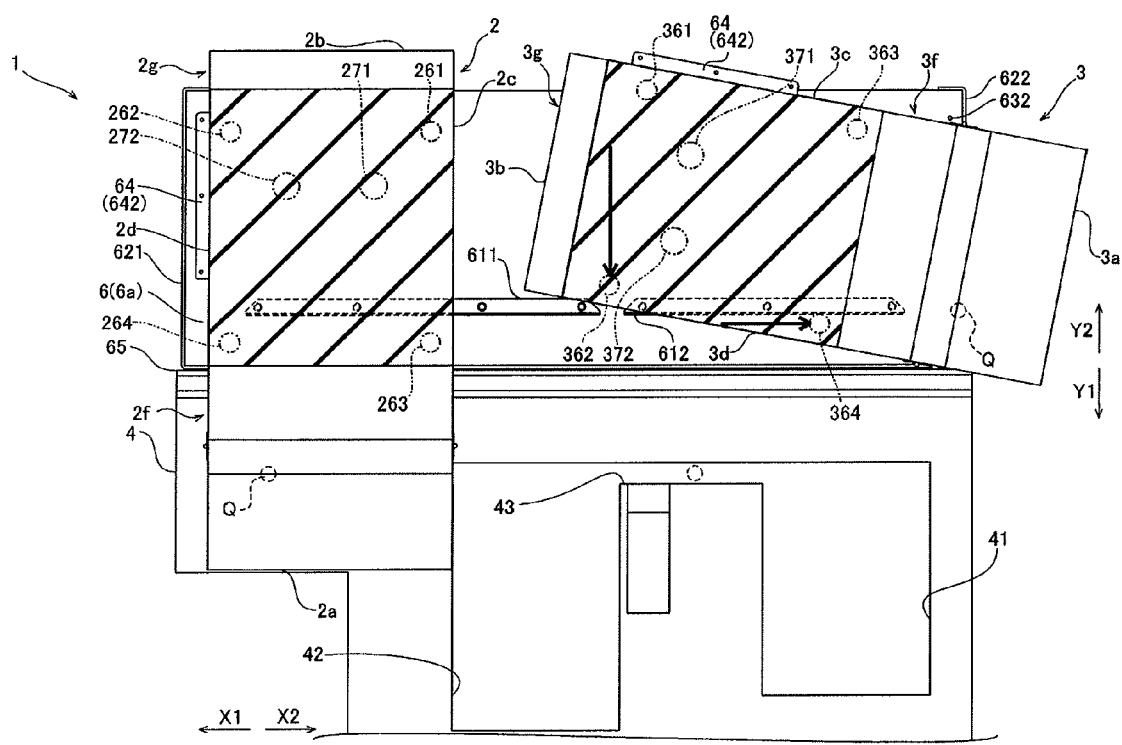
FIG. 20 is a diagram for describing the movements, to the maintenance work position and to the second loading position, of the measurement units of the blood analyzer according to the embodiment of the present invention.

Then, as shown in FIG. 20, the rotation of the second measurement unit 3 in the R2 direction (see FIG. 19) is continued to further move the second measurement unit 3 in the X2 direction. At this point, the ball caster 362 on the back face 3b side of the second measurement unit 3 is moved to the vicinity of an area between the first guides 611 and 612.

Subsequently, as shown in FIG. 21, the ball caster 362 on the back face 3b side of the second measurement unit 3 is passed through the interval between the first guides 611 and 612 and moved toward the front side (in the Y1 direction). As a result, the orientation of the second measurement unit 3 is changed by approximately 90 degrees, and the second measurement unit 3 is rotated sideways such that the other side face 3d is positioned on the front side (Y1 direction side).

Figure 22:
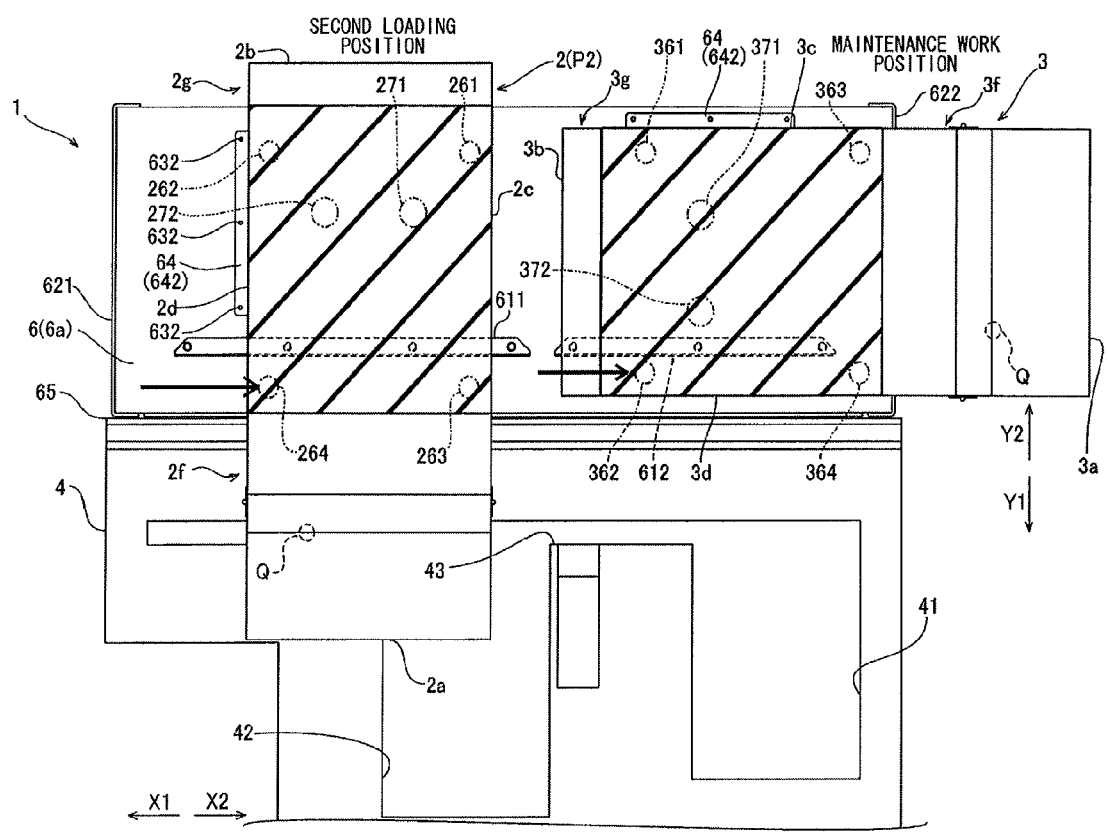
FIG. 22 is a diagram for describing the movements, to the maintenance work position and to the second loading position, of the measurement units of the blood analyzer according to the embodiment of the present invention.

Thereafter, as shown in FIG. 22, the second measurement unit 3 and the first measurement unit 2 are both moved in the X2 direction. In this manner, the second measurement unit 3 is disposed in such a maintenance work position that the other side face 3d is positioned on the front side (Y1 direction side). Note that also during the movement to this maintenance work position, the second measurement unit 3 is moved without falling off the base 6, owing to the restriction by the second guide 622. Further, the first measurement unit 2 having withdrawn to the edge of the X1 direction side is moved to the second loading position P2.

Next, the protrusion (not shown) on the front face 2a of the first measurement unit 2 is inserted into the corresponding second positioning hole 653 of the front face fixing member 65, whereby the first measurement unit 2 is positioned in the second loading position P2. Then, the first measurement unit 2, which has been positioned in the second loading position P2, is fixed in the second loading position P2 via the front face fixing member 65 and the side face fixing member 64. As a result, the first measurement unit 2 becomes able to continue the sample measurement operation in the second loading position P2.

As described above, as shown in FIG. 22, the maintenance work is performed on the second measurement unit 3 disposed in the maintenance work position, and at the same time, the first measurement unit 2 fixed in the second loading position can be loaded with sample containers 100 transported thereto and continue the measurement of the samples. Further, after the maintenance work on the second measurement unit 3 has been completed, the fixedness of the first measurement unit 2 is released again and the first measurement unit 2 is withdrawn to the edge of the X1 direction side, and then the second measurement unit 3 is returned to the first loading position P1. Thereafter, the first measurement unit 2 is moved to the first loading position P1 and each measurement unit is fixed in the first loading position P1. Then, the measurement in the proper position (first loading position P1) is resumed.

The above description regarding the movement of each measurement unit describes rectilinear movement and rotational movement separately for the sake of convenience. However, each measurement unit is capable of freely moving in the X and Y directions and rotating, by using the ball casters. Therefore, in practice, each measurement unit may undergo rotational movement while moving rectilinearly.

As is clear from FIGS. 14 to 22, each measurement unit is capable of freely rotate in the X and Y directions by using the ball casters. Therefore, at the time of maintenance work, the maintenance work can be performed by moving the measurement unit that is a subject of the maintenance work to any position or into any orientation different from those shown in the diagrams. The movement to the maintenance work position can be performed within the movement area that is restricted by the first guides 611 and 612 and the second guides 621 and 622. Although the above description describes an example in which the second measurement unit 3 is moved to the maintenance work position, the first measurement unit 2 can be moved in the same manner.

Further, in the present embodiment, the ball caster 361 of the second measurement unit 3 can be disposed in a position that is displaced from the base 6, as shown in FIGS. 16 and 19. Also in this case, the movement area is restricted as a result of the ball caster 364 of the second measurement unit 3 being in contact with the first guide 612 on the Y1 direction side. Therefore, the second measurement unit 3 is not further moved in the Y2 direction, and does not fall off the base 6, accordingly. At this point, if a weight is applied to the second measurement unit 3 from the above in the Z2 direction (see FIG. 1), there is a possibility that the second measurement unit 3 becomes inclined with respect to the base 6 since the ball caster 361 is displaced from the base 6. In this case, the inclination restricting member 371 having the downward projection height H2 that is slightly smaller than the downward projection height of the ball casters comes into contact with the base 6, thereby restricting the inclination.

Still further, as shown in FIG. 23, the removal position Q of the first measurement unit 2 disposed in the second loading position P2 is located above the tenth container (tenth container counted from the X1 direction side) in the rack 101 having been transported to the vicinity of the edge of the X1 direction side of the rack transporter 43. Also, the removal position Q of the second measurement unit 3 disposed in the second loading position P2 is located above the first container (first container counted from the X1 direction side) in the rack 101 having been transported to the vicinity of the edge of the X2 direction side of the rack transporter 43. That is, all the sample containers 100 accommodated in the rack 101 can be transported to the removal position Q of the first measurement unit 2 or the second measurement unit 3, which has been moved to the second loading position P2. Accordingly, the first measurement unit 2 or the second measurement unit 3, which is fixed in the second loading position P2, can be loaded with all the ten sample containers 100 accommodated in the rack 101. Thus, the second loading position P2 of each measurement unit is determined based on a positional relationship between the removal position Q of each measurement unit and the samples transported thereto.

Next, operations, which are performed by the blood analyzer 1 of the present embodiment during measurement processes based on the measurement process programs 54a and 54b, will be described with reference to FIGS. 2 and 8 to 10. Note that since the first measurement unit 2 and the second measurement unit 3 measure components that are analysis subjects in the same manner, a case where the first measurement unit 2 measures components that are analysis subjects is described below as a representative case.

As shown in FIGS. 8 and 9, the rack 101 is sent to be positioned between the two protrusions 431d of the first belt 431, and the rack 101 is moved in the X1 direction (forward direction). Then, as shown in FIG. 2, the presence/absence detection sensor 45 detects presence/absence of the first sample container 100 accommodated in the rack 101 moved in the X1 direction. Note that a detection result obtained by the presence/absence detection sensor 45, and bar code information read by the bar code readers 44, 256 and 356, are transmitted to the host computer 7 at any time, as necessary.

Then, the rack 101 is moved to the removal position Q (see FIG. 2) at which the hand part 251 of the first measurement unit 2 removes the first sample container 100 from the rack 101 (i.e., the first sample container 100 is transported to the first measurement unit 2). Thereafter, the hand part 251 of the first measurement unit 2 removes the first sample container 100 from the rack 101. At this point, the rack 101 is stationary in such a position that the position of the first sample container 100 coincides with the removal position Q. In the first measurement unit 2, the sample in the first sample container 100 held by the hand part 251 is agitated, and the rack 101 from which the first sample container 100 has been removed is moved in a reverse direction that is the opposite direction to the forward direction. The first sample container 100 removed by the hand part 251 is transported to the aspirating position (see FIG. 2) by the sample container moving part 255.

In the aspirating position, the sample aspirator 21 aspirates the sample from the first sample container 100. Here, the rack 101 is moved in the X2 direction until the second sample container 100 reaches the removal position Q (see FIG. 2) at which the hand part 351 of the second measurement unit 3 removes the second sample container 100 from the rack 101 (i.e., the second sample container 100 is transported to the second measurement unit 3). Then, the second sample container 100 is removed from the rack 101 by the hand part 351 of the second measurement unit 3, and transported to the aspirating position (see FIG. 2) by the sample container moving part 355. Then, in the first measurement unit 2, the specimen preparation section 22 prepares a detection specimen from the aspirated sample, and the detector 23 detects, from the detection specimen, components that are analysis subjects.

Thereafter, the rack 101 is moved in the X1 direction (forward direction), and then the first sample container 100 is returned from the first measurement unit 2 to a container accommodating portion 101b of the rack 101, which is the original storing position of the first container 100. In this manner, the sample containers 100 accommodated in the rack 101 are sequentially removed by the measurement units. Then, measurement data is transmitted from the first measurement unit 2 to the control apparatus 5. Subsequently, based on the measurement data transmitted from the first measurement unit 2, the control section 51 analyzes the components that are analysis subjects.

As described above in the present embodiment, the measurement units (the first measurement unit 2 and the second measurement unit 3) are configured such that each measurement unit can be moved on the base 6 in order to change the orientation thereof, and that the movement area of the measurement units is restricted. Consequently, even when the maintenance work is performed on the one side face 2c and the other side face 3d of the respective measurement units, which are opposed to each other, the space for the maintenance work can be widened by changing the orientation of one of the measurement units. Accordingly, the blood analyzer 1 can be reduced in size while securing sufficient space for performing the maintenance work on each measurement unit.

Further, in the present embodiment, the first guides 611 and 612 and the second guides 621 and 622 restrict the movement area of the measurement units (the first measurement unit 2 and the second measurement unit 3) that are in a rotatable state on the base 6, to such an area as to prevent each measurement unit from falling off the base 6. Accordingly, each measurement unit can be rotated without falling off the base 6, and one of the side faces of the first measurement unit 2 and the second measurement unit 3 that are opposed to each other (one of the one side face 2c of the first measurement unit 2 and the other side face 3d of the second measurement unit 3) can be directed to the operator side (Y1 direction side). This allows the workability in the case of performing the maintenance work on the side faces of the measurement units, to be improved.

Still further, in the present embodiment, the measurement units (the first measurement unit 2 and the second measurement unit 3) are configured to be able to not only rotate on the base 6 but also move in directions (X directions) along which the measurement units are arranged. As a result, at the time of maintenance work, the respective measurement units are moved in the X directions on the base 6 to increase a distance between the measurement units that are adjacent to each other. In this manner, space for the measurement units to rotate can be readily obtained.

Still further, in the present embodiment, the first measurement unit 2 and the second measurement unit 3 are provided with the ball casters 261 to 264 and the ball casters 361 to 364, respectively, for the purpose of smoothing the movements thereof on the base 6. Accordingly, the orientation of the measurement unit 2(3) on the base 6 can be readily changed, using the ball casters 261 to 264 (361 to 364), within the movement area restricted by the first guides 611 and 612 and the second guides 621 and 622. As a result, space for the maintenance work can be readily obtained.

Still further, in the present embodiment, the measurement unit 2(3) is provided with the inclination restricting members 271 and 272 (371 and 372) for restricting the inclination thereof with respect to the base 6. Accordingly, even in the case where one of the ball casters 261 to 264 (361 to 364) of the measurement unit 2(3) is displaced from the base 6, causing insufficient support for the measurement unit 2(3), the inclination restricting members 271 and 272 (371 and 372) can suppress the inclination of the measurement unit 2(3).

Still further, in the present embodiment, the inclination restricting members 271 and 272 (371 and 372) having the smaller downward projection height H2 than the downward projection height H1 of the ball casters are provided on the bottom face 2e (3e) of the measurement unit 2(3). Accordingly, when the measurement unit 2(3) is moved on the base 6, the inclination restricting members 271 and 272 (371 and 372) do not hinder the movement of the measurement unit 2(3). Moreover, in the case where the measurement unit 2(3) becomes inclined with respect to the base 6 when one of the ball casters 261 to 264 (361 to 364) is displaced from the base 6, the inclination restricting members 271 and 272 (371 and 372) come into contact with the base 6. In this manner, the inclination of each measurement unit can be prevented from becoming substantial.

Still further, in the present embodiment, the first guides 611 and 612 and the second guides 621 and 622 come into contact with the ball casters (261 to 264 and 361 to 364) of the measurement units, thereby restricting the movement area of the measurement units. Accordingly, by only providing the first guides 611 and 612 and the second guides 621 and 622 at desired positions on the base 6, the movement area on the base 6, in which the measurement units move using the ball casters (261 to 264 and 361 to 364), can be restricted desirably.

Still further, in the present embodiment, the first guides 611 and 612 are provided on the base 6 so as to extend in a direction (X direction) that is along the transporting direction of the sample containers 100 (rack 101), and the second guides 621 and 622 are provided at the periphery of the base 6 so as to extend in a direction (Y direction) that is perpendicular to the transporting direction. Accordingly, by using the first guides 611 and 612 and the second guides 621 and 622, the movements of the measurement units can be restricted with respect to both the direction (X direction) that is along the transporting direction of the sample containers 100 (rack 101) and the direction (Y direction) that is perpendicular to the transporting direction of the sample containers 100 (rack 101).

Still further, in the present embodiment, the first guides 611 and 612 are each configured to have a length greater than both the interval D1 and the interval D2, each of which is an interval between two adjacent ball casters among the four ball casters 261 to 264 (361 to 364). Accordingly, the measurement unit 2(3) is configured such that when the measurement unit 2(3) is disposed in the first loading position P1 or in the second loading position P2, the two adjacent ball casters 263(363) and 264(364) are arranged between the first guide 611(612) and the sample transporting apparatus 4. As a result, even in the case where the measurement unit 2(3) is moved from the first loading position P1 or the second loading position P2 in such a direction as to become distant from the sample transporting apparatus 4, the first guide 611(612) assuredly comes into contact with the ball caster 263(363) and 264(364), whereby the movement of the measurement unit 2(3) can be restricted.

Still further, in the present embodiment, the first guides 611 and 612 are provided corresponding to the measurement units 2 and 3, respectively, and the first guides 611 and 612 are provided such that the interval between the first guides 611 and 612 is the interval D7 that allows the ball casters 261 to 264 (361 to 364) to pass therethrough when the measurement unit 2(3) is rotated. Accordingly, the ball casters 261 to 264 (361 to 364) can be moved across both the area on the Y1 direction side and the area on the Y2 direction side that are parted by the first guides. As a result, the measurement units can be readily rotated while restricting the movement area of the measurement units.

Note that the embodiment disclosed herein is merely illustrative in all aspects and should not be recognized as being restrictive. The scope of the present invention is defined by the scope of the claims rather than by the description of the above embodiment, and includes meaning equivalent to the scope of the claims and all modifications within the scope.

For example, the above embodiment describes the blood analyzer 1 that includes the two measurement units (the first measurement unit 2 and the second measurement unit 3). However, the present invention is not limited thereto. The sample processing system of the present invention may include three or more measurement units.

Further, the above embodiment describes an example in which the first measurement unit 2 and the second measurement unit 3 are capable of moving and rotating on the base 6 by using the ball casters 261 to 264 and the ball casters 361 to 364 that smooth the movements of the first measurement unit 2 and the second measurement unit 3, respectively. However, the present invention is not limited thereto. The movements of the respective measurement units may be smoothed by different movement smoothing members from the ball casters. For example, a sheet member may be provided which reduces the friction between the bottom face 2e (3e) and the top face 6a of the base 6 and thereby smooths the movement of the measurement unit 2(3). Alternatively, each measurement unit may be provided with casters that have different wheels from those of the ball casters.

Still further, the above embodiment describes an example in which each measurement unit is configured to be fixed in the first loading position P1 by screw connection at the first fixing holes 631 and 652, and fixed in the second loading position P2 by screw connection at the second fixing holes 632 and 654. However, the present invention is not limited thereto. Each measurement unit may be fixed in the first loading position or the second loading position in a different manner from the screw connection. For example, engaging portions may be provided on the base and on the front face fixing member, and each measurement unit may be configured to be fixed when the fixing member and the front face thereof are engaged with the engaging portions.

Still further, the above embodiment describes an example in which each measurement unit is configured to be fixed to the base 6 via the side face fixing member 64 and the front face fixing member 65. However, the present invention is not limited thereto. Each measurement unit may be configured to be directly fixed to the base without using fixing members.

Still further, the above embodiment describes an example in which the first measurement unit 2 and the second measurement unit 3 are configured to be able to move and rotate on the base 6. However, the present invention is not limited thereto. It is sufficient that the first and second measurement units are able to, at least, move to change their orientations. For example, shafts may be provided on the base for allowing the respective measurement units to rotate. Alternatively, the respective measurement units may be provided on rotating tables on the base.

Still further, the above embodiment describes a configuration example in which the movements of the measurement units are restricted by the first guides and second guides provided on the base 6 and by the ball casters provided on the measurement units. However, the present invention is not limited thereto. For example, on the base 6, rails may be provided in advance along paths on which the ball casters move when the orientations of the measurement units are changed. The movements of the measurement units may be restricted by causing the ball casters to move along the rails in predetermined directions.

Still further, the above embodiment describes an example in which the first guides 611 and 612 are provided such that, when viewed in a plan view, the first guides 611 and 612 extend along the transporting direction (X direction) of the rack 101 (sample containers 100), and the second guides 621 and 622 are provided such that, when viewed in a plan view, the second guides 621 and 622 extend, along both the side faces on the X direction sides of the base 6, in a direction (Y direction) perpendicular to the transporting direction of the rack 101 (sample containers 100). However, the present invention is not limited thereto. The number of first guides and the number of second guides may each be three or more. Also, the arrangement of the first guides and the second guides may be changed such that the first guides and the second guides are arranged so as to surround each measurement unit. Further, the shapes of the first guides and the second guides may be changed. For example, the first guides and the second guides may be formed in curved shapes.

Still further, the above embodiment describes an example in which the second loading position P2 allows each measurement unit to be loaded with all the sample containers 100 (ten containers in the present embodiment) accommodated in the rack 101. However, the present invention is not limited thereto. The second loading position may allow each measurement unit to be loaded with only a part of the plurality of sample containers accommodated in the rack. To be specific, the second loading position may allow each measurement unit to be loaded with nine or less sample containers 100 among the sample containers accommodated in the rack 101.

Still further, the above embodiment describes a base 6 on which the first measurement unit 2 and the second measurement unit 3 is placed. The base 6 is provided with the movement restricting section for the first measurement unit 2 and the second measurement unit 3. However the present invention is not limited thereto. The sample processing system may comprise a plurality of bases for each measurement unit. In this case, a base on which the first measurement unit 2 is placed may be provided with the first guides 611 and the second guides 621, and another base on which the second measurement unit 3 may be provided with the first guides 612 and the second guides 622.

What is claimed is:

1. A sample processing system comprising:
   a plurality of sample processing apparatuses disposed on a base; and
   a transporting apparatus configured to transport samples held in a rack to the plurality of sample processing apparatuses, wherein
   the base on which the plurality of sample processing apparatuses are placed has a movement restricting section configured to restrict a movement area of at least one of the plurality of sample processing apparatuses and to allow the at least one of the plurality of sample processing apparatuses to move so as to change orientation of the at least one of the plurality of sample processing apparatuses relative to the base, and
   the transporting apparatus is further configured to transport the samples, while the orientation of the at least one of the plurality of sample processing apparatuses is changed, to another of the plurality of sample processing apparatuses.

2. The sample processing system of claim 1, wherein the movement restricting section restricts the movement area while allowing the at least one of the plurality of sample processing apparatuses to further move on the base in the direction along which the plurality of sample processing apparatuses are arranged.

3. The sample processing system of claim 1, wherein the at least one of the plurality of sample processing apparatuses is allowed, in the restricted movement area, to move and rotate so as to partly protrude from the base, when viewed in a plan view, without falling off the base.

4. The sample processing system of claim 1, wherein the at least one of the plurality of sample processing apparatuses comprises a movement smoothing member for allowing the at least one of the plurality of sample processing apparatuses to move smoothly on the base.

5. The sample processing system of claim 1, wherein the at least one of the plurality of sample processing apparatuses comprises an inclination restricting member for restricting inclinations of the at least one of the plurality of sample processing apparatuses with respect to the base, wherein
   when the at least one of the plurality of sample processing apparatuses is moved to a position on which the at least one of the plurality of sample processing apparatuses partly protrude from the base when viewed in a plan view, the inclination restricting member restricts the inclination of the at least one of the plurality of sample processing apparatuses with respect to the base.

6. The sample processing system of claim 5, wherein the at least one of the plurality of sample processing apparatuses comprises a movement smoothing member for allowing the at least one of the plurality of sample processing apparatuses to move smoothly on the base, and
   the inclination restricting member has a smaller downward projection height than that of the movement smoothing member.

7. The sample processing system of claim 1, wherein the base comprises:
   first fixing portion for fixing the at least one of the plurality of sample processing apparatuses in a first loading position in which the at least one of the plurality of sample processing apparatuses is able to be loaded with a sample transported by the transporting apparatus; and
   second fixing portion for fixing the at least one of the plurality of sample processing apparatuses in a second loading position which is different from the first loading position and in which the at least one of the plurality of sample processing apparatuses is able to be loaded with the sample transported by the transporting apparatus.

8. The sample processing system of claim 1, wherein the movement restricting section comprises a restricting member disposed on the base, and
   the restricting member restricts the movement area of the at least one of the plurality of sample processing apparatuses by being in contact with a part of the sample processing apparatus.

9. The sample processing system of claim 8, wherein the restricting member comprises:
   a first restricting member for restricting movement, in a first direction, of the at least one of the plurality of sample processing apparatuses on the base, wherein the first direction is a direction that is perpendicular to the direction in which the samples are transported by the transporting apparatus; and
   a second restricting member for restricting movement, in a second direction, of the at least one of the plurality of sample processing apparatuses on the base, wherein the second direction is a direction along the direction in which the samples are transported.

10. The sample processing system of claim 9, wherein the at least one of the plurality of sample processing apparatuses comprises, on a bottom face thereof, a plurality of movement smoothing members for allowing the at least one of the plurality of sample processing apparatuses to move smoothly on the base,
   the first restricting member is configured to have a length greater than an interval between two adjacent movement smoothing members among the plurality of movement smoothing members, and
   the two adjacent movement smoothing members are arranged between the first restricting member and the transporting apparatus when each sample processing apparatus is in a state of being able to be loaded with a sample transported by the transporting apparatus.

11. The sample processing system of claim 1, wherein the plurality of sample processing apparatuses includes a first sample processing apparatus and a second sample processing apparatus which are placed on the base; and
   the transporting apparatus is configured to transport the rack in first direction from the first sample processing apparatus to the second sample processing apparatus and in second direction opposite to the first direction.

12. The sample processing system of claim 11, wherein the first sample processing apparatus includes a first detector and the second sample processing apparatus includes a second detector, wherein the first detector and the second detector are configured to detect components of the samples using same detection method.

* * * * *